(12) United States Patent
Etcheberrigaray et al.

(10) Patent No.: US 9,539,235 B2
(45) Date of Patent: *Jan. 10, 2017

(54) METHODS FOR ALZHEIMER'S DISEASE TREATMENT AND COGNITIVE ENHANCEMENT

(71) Applicant: BLANCHETTE ROCKEFELLER NEUROSCIENCES INSTITUTE, Morgantown, WV (US)

(72) Inventors: Rene Etcheberrigaray, Bethesda, MD (US); Daniel L. Alkon, Bethesda, MD (US)

(73) Assignee: COGNITIVE RESEARCH ENTERPRISES, INC, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,161

(22) Filed: Mar. 27, 2013

(65) Prior Publication Data
US 2013/0281522 A1    Oct. 24, 2013

Related U.S. Application Data

(60) Continuation of application No. 10/933,536, filed on Sep. 3, 2004, now abandoned, which is a division of
(Continued)

(51) Int. Cl.
*A61K 31/335*    (2006.01)
*A61K 31/35*    (2006.01)
(Continued)

(52) U.S. Cl.
CPC .......... *A61K 31/365* (2013.01); *A61K 9/0053* (2013.01); *A61K 31/00* (2013.01); *A61K 31/366* (2013.01)

(58) Field of Classification Search
CPC ............................ A61K 31/365; A61K 31/366
(Continued)

(56) References Cited

U.S. PATENT DOCUMENTS 4,560,774 A    12/1985  Pettit et al.
4,611,066 A     9/1986  Pettit et al.
(Continued)

FOREIGN PATENT DOCUMENTS

CA    2401452    3/2003
DE    A-3827974   2/1990
(Continued)

OTHER PUBLICATIONS

Burry, R. W., "PKC Activators (Phorbol Ester or Bryostatin) Stimulate Outgrowh of NGF-Dependent Neurites in a Subline of PC12 Cells," Journal of Neurosciences Research, 53:214-222 (1998).
(Continued)

*Primary Examiner* — Shengjun Wang
(74) *Attorney, Agent, or Firm* — Finnegan, Henderson, Farabow, Garrett & Dunner LLP

(57) ABSTRACT

The present invention relates to compositions and methods to modulate α-secretase and/or to improve cognitive ability. The invention further relates the improved/enhanced cognitive ability in diseased individuals, particularly Alzheimer's Disease patients, and treatment thereof through increased sAPP production. Macrocyclic lactones (i.e. bryostatin class and neristatin class) are compounds preferred for use with the present composition. The present invention also provides methods for increasing the generation of non-amyloidogenic soluble APP comprising the activation of protein kinase C (PKC) by administering an effective amount of PKC activator(s).

2 Claims, 6 Drawing Sheets

Related U.S. Application Data application No. 10/167,491, filed on Jun. 13, 2002, now Pat. No. 6,825,229.

(60) Provisional application No. 60/362,080, filed on Mar. 7, 2002.

(51) Int. Cl.
*A61K 31/365* (2006.01)
*A61K 31/00* (2006.01)
*A61K 31/366* (2006.01)
*A61K 9/00* (2006.01)

(58) Field of Classification Search
USPC ........................................ 514/449, 450, 451
See application file for complete search history.

(56) References Cited

U.S. PATENT DOCUMENTS

| | | | |
|---|---|---|---|
| 4,833,139 A | 5/1989 | Martin | |
| 4,833,257 A | 5/1989 | Pettit et al. | |
| 5,072,004 A | 12/1991 | Pettit | |
| 5,196,447 A | 3/1993 | Pettit et al. | |
| 5,288,514 A | 2/1994 | Ellman | |
| 5,359,115 A | 10/1994 | Campbell et al. | |
| 5,362,899 A | 11/1994 | Campbell | |
| 5,393,897 A | 2/1995 | Pettit et al. | |
| 5,430,053 A | 7/1995 | Pettit et al. | |
| 5,545,636 A | 8/1996 | Health et al. | |
| 5,578,590 A | 11/1996 | Grunicke et al. | |
| 5,580,748 A | 12/1996 | Alkon et al. | |
| 5,625,232 A | 4/1997 | Numata et al. | |
| 5,770,593 A | 6/1998 | Grunicke et al. | |
| 5,891,870 A | 4/1999 | Driedger et al. | |
| 5,891,906 A | 4/1999 | Driedger et al. | |
| 5,955,501 A | 9/1999 | Driedger et al. | |
| 5,962,498 A | 10/1999 | Driedger et al. | |
| 5,962,504 A | 10/1999 | Kozikowski et al. | |
| 5,981,165 A | 11/1999 | Weiss et al. | |
| 6,043,270 A * | 3/2000 | Driedger et al. | 514/450 |
| 6,080,582 A | 6/2000 | Alkon et al. | |
| 6,080,784 A | 6/2000 | Driedger et al. | |
| 6,187,568 B1 | 2/2001 | Nishida et al. | |
| 6,242,479 B1 | 6/2001 | Wechter | |
| 6,407,058 B1 | 6/2002 | Staddon et al. | |
| 6,458,373 B1 | 10/2002 | Lambert et al. | |
| 6,624,189 B2 | 9/2003 | Wender et al. | |
| 6,825,229 B2 * | 11/2004 | Etcheberrigaray et al. | 514/451 |
| 7,803,400 B2 | 9/2010 | Nelson et al. | |
| 7,977,377 B2 | 7/2011 | Sun et al. | |
| 2002/0193360 A1 | 12/2002 | Villalobos | |
| 2003/0050302 A1 | 3/2003 | Etcheberrigaray et al. | |
| 2003/0077335 A1 | 4/2003 | Richardson et al. | |
| 2003/0171356 A1 | 9/2003 | Etcheberrigaray et al. | |
| 2003/0171385 A1 | 9/2003 | Alkon et al. | |
| 2005/0037984 A1 | 2/2005 | Etcheberrigaray et al. | |
| 2005/0065205 A1 | 3/2005 | Alkon | |
| 2005/0075393 A1 | 4/2005 | Nishizaki et al. | |

FOREIGN PATENT DOCUMENTS

| | | |
|---|---|---|
| DE | 19943198 | 3/2001 |
| EP | 0 115 472 | 8/1984 |
| EP | 0 324 574 A2 | 7/1989 |
| EP | 0 413 191 | 2/1991 |
| EP | 0 432 856 | 6/1991 |
| EP | 1 195 159 | 4/2002 |
| JP | 06-279311 | 10/1994 |
| JP | 2001-240581 | 9/2001 |
| JP | 2003-146883 | 5/2003 |
| WO | WO 91/07087 | 5/1991 |
| WO | WO 92/10092 | 6/1992 |
| WO | WO 93/09668 | 5/1993 |
| WO | WO 93/20242 | 10/1993 |
| WO | WO 94/08051 | 4/1994 |
| WO | WO 96/35417 | 11/1996 |
| WO | WO 97/43268 | 11/1997 |
| WO | WO 98/32464 | 7/1998 |
| WO | WO 99/59597 | 11/1999 |
| WO | WO 01/83449 | 8/2001 |
| WO | WO 01/68137 | 9/2001 |
| WO | WO 01/93883 | 12/2001 |
| WO | WO 02/50013 | 6/2002 |
| WO | WO 02/083877 | 10/2002 |
| WO | WO 02/086106 | 10/2002 |
| WO | WO 02/087423 A3 | 11/2002 |
| WO | WO 03/075850 | 9/2003 |
| WO | WO 03/075850 A2 | 9/2003 |
| WO | WO 03/075930 | 9/2003 |
| WO | WO 2004/004641 | 1/2004 |
| WO | WO 2004/004641 A2 | 1/2004 |
| WO | WO 2004/047857 | 6/2004 |
| WO | WO 2005/032474 | 4/2005 |
| WO | WO 2005/115548 | 12/2005 |
| WO | WO 2006/031337 | 3/2006 |
| WO | WO 2007/016202 | 2/2007 |
| WO | WO 2007/044094 | 4/2007 |
| WO | WO 2008/013573 | 1/2008 |
| WO | WO 2008/100449 | 8/2008 |

OTHER PUBLICATIONS

Connolly, "Fibroblast Models of Neurological Disorders: Fluorescence Measurement Studies," TIPS, 19:171-177 (1998).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Etcheberrigaray et al., "Therapeutic effect of PKC activators in Alzheimer's disease transgenic mice", PNAS, 01(30):11141-11146 (2004).
Final Office Action mailed Nov. 23, 2010, in U.S. Appl. No. 11/802,842.
Final Office Action mailed Mar. 5, 2009, in U.S. Appl. No. 10/933,536.
Final Office Action mailed May 13, 2010, in U.S. Appl. No. 12/068,742.
Ibarreta et al., "Benzolactam (BL) Enhances sAPP Secretion in Fibroblasts and in PC12 Cells," Ageing, 10(5):1035-1040 (1999).
Mutter et al., "Chemistry and Clinical Biology of the Bryostatins," Bioorganic & Medicinal Chemistry, 8:1841-1860 (2000).
Office Action (Restriction Requirement) mailed Jun. 28, 2010, in U.S. Appl. No. 11/698,953.
Office Action mailed Jan. 30, 2008, in U.S. Appl. No. 10/933,536.
Office Action mailed May 26, 2010, in U.S. Appl. No. 11/802,842.
Office Action mailed May 28, 2008, in U.S. Appl. No. 10/933,536.
Office Action mailed Sep. 18, 2012, in U.S. Appl. No. 13/042,892.
Office Action mailed Sep. 5, 2012, in U.S. Appl. No. 12/538,245.
Office Action (Restriction Requirement) mailed Jun. 23, 2009, in U.S. Appl. No. 12/068,742.
Office Action (Restriction Requirement) mailed Mar. 7, 2011, in U.S. Appl. No. 10/594,420.
Office Action mailed Aug. 15, 2011, in U.S. Appl. No. 10/594,420.
Office Action mailed Feb. 4, 2010, in U.S. Appl. No. 11/802,842.
Office Action mailed Jan. 31, 2012, issued in U.S. Appl. No. 12/851,222.
Office Action mailed Jul. 20, 2011, in U.S. Appl. No. 11/802,723.
Office Action mailed Jul. 7, 2011, in U.S. Appl. No. 11/698,953.
Office Action mailed May 4, 2012, in U.S. Appl. No. 13/152,616.
Office Action mailed Oct. 21, 2009, in U.S. Appl. No. 12/068,742.
Zhang et al., "Preclinical Pharmacology of the Natural Product Anticancer Agent Bryostatin 1, an Activator of Protein Kinase C1," Cancer Research, 56:802-808 (1996).
Abramets et al., "Behavioral Depression-Related Modifications of the Properties of Glutamatergic Synapses in the Basolateral Amygdalar Nucleus in Rats," Neurophysiology,34(4):283-293 (2002).

(56) References Cited

OTHER PUBLICATIONS

Agranoff et al., "Actinomycin D Blocks Formation of Memory of Shock-Avoidance in Goldfish," Science, 158 (Dec. 22, 1967).
Alkon et al., "Reduction of two voltage-dependent K+ currents mediates retention of a learned association", Behav. Neural Biol., 44: .278-300 (1985).
Alkon et al., "Regulation of Hermissenda K+ Channels by Cytoplasmic and Membrane-Associated C-Kinase" J. Neurochem., 51(3):903-916 (1988).
Alkon et al., Protein Synthesis Required for Long-Term Memory is Induced by PKC Activation on Days Before Associative Learning, Proc. Natl. Acad. Sci. USA, 102(45):16432-16437 (2005).
Alkon, D.L., "Calcium-mediated reduction of ionic currents: A biophysical memory trace," Science, 226: 1037-1045 (1984).
Ashendel et al., "Protein Kinase Activity Associated With a Phorbol Ester Receptor Purified from Mouse Brain", Cancer Res., 43: 4333-4337 (1983).
Bank et al., "Classical Conditioning Induces Long-Term Translocation of Protein Kinase C in Rabbit Hippocampal CA1 Cells", Proc. Natl. Acad. Sci. USA, 85:1988-1992 (Mar. 1988).
Barbas et al., "Multiple Serotonergic Mechanisms Contributing to Sensitization in Aplysia: Evidence of Diverse Serotonin Receptor Subtypes," Serotonin & Memory/Review, 10:373-386 (2003).
Battaini, "Protein Kinase C Isoforms as Therapeutic Targets in Nervous System Disease States," Pharmacological Research, 44(5):353-361 (2001).
Bennett et al., "Expression Analysis of BACE2 in Brain and Peripheral Tissues," The Journal of Biological Chemistry, 275(27): 29647-20651 (2000).
Bergamaschi et al., "Defective Phorbol Ester-Stimulated Secretion of B-Amyloid Precursor Protein from Alzheimer's Disease Fibrobiasts," Neuroscience Letters, 201:1-4 (1995).
Bergold et al., "Protein Synthesis During Acquisition of Long-Term Facilitation is Needed for the Persistent Loss of Regulatory Subunits of the Aplysia cAMP-Dependent Protein Kinase", Proc. Natl. Acad. Sci. USA, 87:3788-3791(May 1990).
Berke et al., "Dopamine and Glutamate Induce Distinct Striatal Splice Forms of Ania-6, an RNA Polymerase II-Associated Cyclin," Neuron, 32:277-287 (Oct. 25, 2001).
Berman et al., "Specific and Differential Activation of Mitogen-Activated Protein Kinase Cascades by Unfamiliar Taste in the Insular Cortex of the Behaving Rat," The Journal of Nueroscience, 18(23);10037-10044 (Dec. 1, 1998).
Besag, "Behavioral Effects of the New Anticonvulsants," Drug Safety, 24(7):513-536 (2001).
Bhagavan et al., "Restoration of TEA-Induced Calcium Responses in Fibroblasts from Alzheimer's Disease Patients by a PKC Activator," Neurobiol. Disease, 5:177-187 (1998).
Birkmayer, "L-Deprenyl Plus L. Phenylalanine in the Treatment of Depression," Journal of Neural Transmission, 59:81-87 (1984).
Blobe et al., "Regulation of Protein Kinase C and Role in Cancer biology," Cancer Metast. Rev., 13:411-431 (1994).
Bondy et al., "The PHA-Induced Calcium Signal in Lymphocytes is Altered After Blockade of K+-Channels in Alzheimer's Disease," J. Psychiat. Res., 30(3):217-227 (1996).
Bouron et al. "Acute Application of the Tricyclic Antidepressant Desipramine Presynaptically Stimulates the Exocytosis of Glutamate in the Hippocampus," Neuroscience, 90(3):729-736, (1999).
Budziszewska et al., "Antidepressant Drugs Inhibit Glucocorticoid Receptor-Mediated Gene Transcription—A Possible Mechanism," British Journal of Pharmacology, 130:1385-1393 (2000).
Burke et al., "Update on Alzheimer's Disease: Promising advances in Detection and Treatment," Postgraduate Medicine, 106(5): 85-95 (1999).
Burry et al., "PKC Activators (Phorbol Ester or Bryostatin) Stimulate Outgrowth of NGF-Dependent Neutrites in a Subline of PC 12 Cells", Journal of Neuroscience Research, 1998, vol. 53, No. 2, pp. 214-222.

Bursell S.E. et al., "Can Protein Kinase C Inhibition and Vitamin E Prevent the Development of Diabetic Vascular Complications?", Diabetes Research and Clinical Practice, 45( 2/03): 169-182 (Jan. 1999).
Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).
Cai et al., "BACE1 is the major β-secretase for Generation of Aβ Peptides by Neurons," Nature Neuroscience 4(3):233-234 (Mar. 2001).
Calingasan et al., "Accumulation of Amyloid Precursor Protein-like Immunoreactivity in Rat Brain in Response to Thiamine Deficiency", Brain Research, 677(1): 50-60 (1995).
Calo et al., "Pharmacology of Nociceptin and its Receptor: a Novel Therapeutic Target", British Journal of Pharmacology, 129:1261-1283 (2000).
Caputi et al., "Increased Secretion of the Amino-Terminal Fragment of Amyloid Precursor Protein in Brains of Rats with a Constitutive Up-Regulation of Protein Kinase C," J. Neurochem., 68(6):2523-2529 (1997).
Casini et al., "Carbonic Anhydrase Activators. The Selective Serotonin Reuptake Inhibitors Fluoxetine, Sertraline and Citalopram Are Strong Activators of Isozymes I and II," Bioorganic & Medicinal Chemistry Letters, 13:2765-2768 (2003).
Cavallaro "Memory-Specific Temporal Profiles of Gene Expression in the Hippocamous", PNAS, 99(25):16279-16284 (Dec. 2002).
Cavallaro et al., "Late Memory-Related Genes in the Hippocampus Revealed by RNA Fingerprinting", Proc. Natl. Acad. Sci. USA, 94:9669-9673 (Sep. 1997).
Certified U.S. Appl. No. 60/392,951.
Chetkovich et al., "N-Methyl-D-Aspartate Receptor Activation Increases cAMP Levels and Voltage-Gated Ca2+ Channel Activity in Area CA1 of Hippocampus", Proc. Natl. Acad. Sci. USA, 88:6467-6471 (Aug. 1991).
Chow, C.K., "Vitamin E Regulation of Mitochondrial Superoxide Generation", Biological Signals and Receptors, 10(1-2): 112-124 (Jan. 2001).
Clamp et al., "The Clinical Developments of Bryostatins", Anti-Cancer Drugs, 13(7): 673-683 (Aug. 2002).
Cole et al., "Decreased Levels of Protein Kinase C in Alzheimer Brain," Brain Research, 452:165-174 (1988).
Collin et al., "Sequential Modification of membrane currents induced by classical conditioning" Biophysical J. 54: 955-961 (1988).
Coughlan et al., "Factors Influencing the Processing and Function of the Amyloid B Precursor Protein—A Potential Therapeutic Target in Alzheimer's Disease?," Pharmacology & Therapeutics, 86:111-144 (2000).
Coull et al., "Altered Brain Protein Kinase C in Depression: a Post-Mortem Study," European Neuropsychopharmacology, 10:283-288 (2000).
Crow et al., "Inhibition of Protein Synthesis Blocks Long-Term Enhancement of Generator Potentials Produced by One-Trial in Vivo Conditioning in Hermissenda", Proc. Natl. Acad. Sci. USA, 87:4490-4494 (Jun. 1990).
Crow et al., "Protein Synthesis-Dependent and mRNA Synthesis-Independent Intermediate Phase of Memory in Hermissenda," The American Physiological Society, Rapid Communication, 82:495-500 (1999).
Davis, "The Mitogen-activated Protein Kinase Signal Transduction Pathway," The Journal of Biological Chemistry, 268(20):14553-14556 (Jul. 15, 1993).
De Lorenzo et al., "Bryostatin-1 Stimulates the Transcription of Cyclooxygenase-2: Evidence for an Activator Protein-1-Dependent Mechanism", Clinical Cancer Research, 9:5036-5043 (2003).
Desdouits et al., "Amyloid β Peptide Formation in Cell-free Preparations," The Journal of Biological Chemistry, 271(40):24670-24674 (1996).
Efthimiopoulos et al., "Intracellular Cyclic AMP Inhibits Constitutive and Phorbol Ester-Stimulated Secretory Cleavage of Amyloid Precursor Protein," J. Neurochem., 67(2):872-875 (1996).
English Translation for JP 2001-240581 (2012).

(56) References Cited

OTHER PUBLICATIONS

English-language Translation for JP 6-279311 dated Jun. 2008.
Epstein et al., "Time Windows for Effects of Protein Synthesis Inhibitors on Pavlovian Conditioning in Hermissenda: Behavioral Aspects", Neurobiology of Learning and Memory, 79:127-131 (2003).
Eriksen, "Linking Work Factors to Neck Myalgia: The Nitric Oxide/Oxygen Ratio Hypothesis", Medical Hypotheses 62:721-726 (2004).
Esler et al., "A Portrait of Alzheimer Secretases—New Features and Familiar Faces," Science, 293:1449-1454 (2001).
Espacenet English Abstract for EP 0 115 472 (2012).
Espacenet English Abstract for JP 2003-146883 (2012).
Etcheberrigaray et al., "Classical conditioning and protein kinase C activation regulate the same single potassium channel in Hermissenda crassicornis photoreceptors", Proc Natl Acad Sci USA, 89: 7184-8, 1992.
European Search Report for EP 0574 9738 dated Sep. 10, 2007.
European Search Report for EP 08 01 0738, dated Feb. 2, 2010.
Extended European Search Report issued in EP 12 00 2638 dated Jun. 19, 2012.
Extended European Search Report issued on EP 12005992.8 dated May 24, 2013.
Ezzeddine et al., "Prolonged Habituation of the Gill-Withdrawal Reflex in Aplysia Depends on Protein Synthesis, Protein Phosphatase Activity, and Postsynaptic Glutamate Receptors," The Journal of Neuroscience, 23(29):9585-9594 (Oct. 22, 2003).
Farley et al., "Protein Kinase C Inhibitors Prevent Induction and Continued Expression of Cell Memory in Hermissenda Type B Photoreceptors", Proc. Natl. Acad. Sci. USA, 88:2016-2020 (Mar. 1991).
Favit et al., "Alzheimer's-specific effects of soluble β-amyloid on protein kinase C- and -γ degradation in human fibroblasts", Cell Biology, 95:5562-5567 (1998).
Ferrari, "Behavioural Pharmacology of Imidazole, a Potential Antidepressant Agent," Arch. Int. Pharmacodyn, 277:303-312 (1985).
Flexner et al., "Effect of Acetoxycyclohemimide and of an Acetoxycyclohemimide-Puromycin Mixture on Cerebral Protein Synthesis and Memory in Mice," Proc. N.A.S., 55:369-374 (1966).
Gabuzda et al., "Inhibition of β-Amyloid Production by Activation of Protein Kinase C," J. Neurochem., 61(6):2326-2329 (1993).
Ghosh et al., "Design of Potent Inhibitors for Human Brain Memapsin 2 (β.-Secretase)," J. Am. Chem. Soc., 122(14):3522-3523 (2000).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Glazer, R.I., "Protein Kinase C in Multidrug Resistance, Neoplastic Transformation, and Differentiation", Protein Kinase C, New York Oxford Oxford University Press, pp. 171-198, (1994).
Goekjian, et al., "Protein Kinase C in the Treatment of Disease: Signal Transduction Pathways, Inhibitors, and Agents in Development," Current Medicinal Chemistry, 6:877-903 (1999).
Gomez et al., "Ca2+ Signaling via the Neuronal Calcium Sensor-1 Regulates Associative Learning and Memory in C. elegans," Neuron, 30:241-248 (Apr. 2001).
Gould et al., "Signaling Networks in the Pathophysiology and Treatment of Mood Disorders," Journal of Psychosomatic Research, 53:687-697 (2002).
Govoni et al., "Cytosol Protein Kinase C Downregulation in Fibroblasts from Alzheimer's Disease Patients," Neurology, 43:2581-2586 (1993).
Gundlfinger et al., "Different Regulation of Purkinje Cell Dendritic Development in Cerebellar Slice Cultures by Protein Kinase Calpha and -beta," Journal of Neurobiology, 57(1):95-109 (Oct. 2003).
Hahn et al., "Abnormalities in Protein Kinase C Signaling and the Pathphysiology of Bipolar Disorder," Bipolar Disorders, 2:81-86 (1999).

Haniu et al., "Characterization of Alzheimer's β-Secretase Protein BACE: A Pepsin Family Member with Unusual Properties," The Journal of Biological Chemistry, 275(28):21099-21106 (2000).
Hardy, "Amyloid, the Presinilins and Alzheimer's Disease," TINS, 20(4): 154-159 (1997).
Hardy, "Molecular Genetics of Alzheimer's Disease," Acta Neurol Scand, Supplemental, 165:13-17 (1996).
Hayes, "Acetozolamide in Bipolar Affective Disorders," Annals of Clinical Psychiatry, 6(2):91-98 (1994).
Hennings et al., "Bryostatin 1, an Activator of Protein Kinase C, Inhibits Tumor Promotion by Phorbol Esters in SENCAR Mouse Skin," Carcinogenesis, 8(9):1343-1346 (1987).
Hickman et al., "Bryostatin 1, A Novel Antineoplastic Agent and Protein Kinase C Activator, Induces Human Myalgia and Muscle Metabolic Defects: A P Magnetic Resonance Spectroscopic Study", British Journal of Cancer, 72(4):998-1003 (1995).
Hoelting et al., "12-0-tetradecanoyl-phorbol-13-acetate (TPA) Counteracts the Anti-Proliferative and Antiinvasive Effects of Tamoxifen in a Metastatic Follicular Thyroid Cancer Cell Line", Proc. Am. Cancer Res., 36: Abstract No. 481 (Mar. 1995).
Hofmann, "The Potential for Isoenzyme-Selective Modulation of Protein Kinase C," The FASEB Journal, 11:649-669 (1997).
House et al., "Protein kinase C contains a pseudosubstrate prototope in its regulatory domain." Science, 238(4834): 1726-1728 (Dec. 1987).
Howe, C. et al., "Differential Effect of the Manipulation of Protein Kinase C Activity on Normal Versus Leukemic Progenitor Cell Response to rGM-CSF", Proc. Am. Assoc. Cancer Res., 30: Abstract No. 244 (Mar. 1989).
Hu et al., "FGF-18, a Novel Member of the Fibroblast Growth Factor Family, Stimulates Hepatic and Intestinal Proliferation," Molecular and Cellular Biology, 18(10):6063-6074 (Oct. 1998).
Hu et al., "Human Fibroblast Growth Factor-18 Stimulates Fibroblast Cell Proliferation and is Mapped to Chromosome 14p11", Oncogene, 18:2635-2642 (1999).
Hug et al., "Protein kinase C isoenzymes: divergence in signal transduction," Biochem J. 291:329-343 (1993).
Hung et al., "Activation of Protein Kinase C Inhibits Cellular Production of the Amyloid β-Protein," The Journal of Biological Chemistry, 268(31): 22959-22962 (1993).
Huynh et al., "Reduced Protein Kinase C Immunoreactivity and Altered Protein Phosphorylation in Alzheimer's Disease Fibroblasts," Arch Neurol 46: 1195-1199 (1989).
Hyden et al., "Brain-Cell Protein Synthesis Specifically Related to Learning", Proceedings of the National Academy of Sciences, 65(4):898-904, (Apr. 1970).
Impey et al., "Making New Connections: Role of ERK/MAP Kinase Signaling in Neuronal Plasticity", Neuron, 23:11-14 (May 1999).
International Preliminary Report on Patentability issued on PCT/US2005/017158, dated Jan. 16, 2007.
International Search Report and Written Opinion for PCT/US2005/028522 dated Apr. 13, 2006.
International Search Report and Written Opinion for PCT/US2008/006158 dated Apr. 9, 2009.
International Search Report and Written Opinion for PCT/US2006/029110 dated Jan. 2, 2007.
International Search Report and Written Opinion for PCTIUS2007/002454 dated Jul. 13, 2007.
International Search Report for PCT/US2003/07101 dated Oct. 17, 2003.
International Search Report for PCT/US2005/017158 dated Dec. 14, 2006.
Ishii et al., "Protein Kinase C activation and its Role in the Development of Vascular Complications in Diabetes Mellitus," J. Mol. Med., 76:21-31 (1998).
Jayson et al.., "A phase I trial of bryostatin 1 in patients with advanced malignancy using a 24 hour infusion," British Journal of Cancer, 72: 461-468 (1995).
Jin et al., "Changes in Protein Kinases in Brain Aging and Alzheimer's Disease," Drugs &Aging, 6(2):136-149 (1995).

(56) References Cited

OTHER PUBLICATIONS

Johnston-Wilson et al., "Disease-specific Alterations in Frontal Cortex Brain Proteins in Schizophrenia, Bipolar Disorder, and Major Depressive Disorder," Molecular Psychiatry, 5:142-149 (2000).
Jolly-Tornetta et al., "Protein Kinase C Regulation of Intracellular and Cell Surface Amyloid Precursor Protein (APP) Cleavage in CHO695 Cells," Biochemistry, 39:15282-15290 (2000).
Jolly-Tornetta et al., Regulation of Amyloid Precursor Protein (APP) Secretion by Protein Kinase Cα in Human Ntera 2 Neurons (NT2N); Biochemistry, 39(25):7428-7435 (2000).
Kanno et al., "The Linoleic Acid Derivative DCP-LA Selectively Activates PKC-ε, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ε", Dept. of Physiology, Hyogo College of Med., Hyogo, Japan, 45(2&3): p. 552 (2006).
Katzman, "Alzheimer's disease," New England Journal of Medicine, 314(15):964-973 (1986).
Katzoff et al., "Nitric Oxide Is Necessary for Multiple Memory Processes after Learning That a Food Is Inedible in Aplysia," The Journal of Neurosciences, 22(21) 9581-9594 (Nov. 1, 2002).
Khan et al., "An Internally Controlled Perifpheral Biomarker for Alzheimer's Disease: Erk1 and Erk2 responses to the Inflammatory Signal Bradykinin," PNAS, 103(35): 13203-13207 (Aug. 29, 2006).
Kikkawa et al., "Calcium-activated, phospholipid-dependent protein kinase from rat brain. Subcellular distribution, purification, and properties." J. Biol. Chem. 257(22): pp. 13341-13348 (1982).
Kikkawa et al., "The Protein Kinase C Family: Heterogeneity and its Implications." Ann. Rev. Biochem, 58: 31-44 (1989).
Kim et al, "Amyloid Precursor Protein Processing is Separately Regulated by Protein Kinase C and Tyrosine Kinase in Human Astrocytes," Neurosci. Letters, 324(3):185-188 (May 2002).
Kinouchi et al., "Conventional Protein Kinase C (PKC)-α and Novel PKCε, But Not -δ, Increase the secretion of an N-Terminal Fragment of Alzheimer's Disease Amyloid Precursor Protein from PKC cDNA Transfected 3Y1 Fibroblasts," FEBS Letters, 364:203-206 (1995).
Kogure, K. et al., "Alpha-Tocopheryl Succinate Activates Protein Kinase C in Cellular and Cell-free Systems", Journal of Nutritional Science and Vitaminology, 49(5): 310-314 (Oct. 2003).
Kornhauser et al., "A Kinase to Remember: Dual Roles for MAP Kinase in Long-Term Memory", Neuron, 18:839-842 (Jun. 1997).
Kosik et al., "Microtubule-associated Protein 2: Monoclonal Antibodies Demonstrate the Selective Incorporation of Certain Epitopes into Alzheimer Neurofibrillary Tangles" Proc. Natl. Acad. USA, 81:7941-7945 (Dec. 1984).
Kozikowski et al., "Modeling, Chemistry, and Biology of the Benzolactam Analogues of Indolactam V (ILV). 2. Identification of the Binding Site of the Benzolactams in the CRD2 Activator-Binding Domain in PKCs and Discovery of an ILV Analogue of Improved Isozyme Selectivity," J. Med. Chem.,40:1316-1326 (1997).
Kravitz et al., "Dietary Supplements of Phenylalanine and Other Amino Acid Precursors of Brain Neuroamines in the Treatment of Depressive Disorders", Journal of the American Osteopathic Associate. 84(1 Suppl):119-123 (Sep. 1984).
Kunisaki et al., "Normalization of diacylglycerol-protein kinase C activation by vitamin E in aorta of diabetic rats and cultured rat smoth muscle cells exposed to elevated glucose levels." Diabetes, 43: 1372-1377 (1994).
Kuzirian et al., "Bryostatin and lactacystin affect PKC activation and long-term memory," Database BIOSIS [Online], Biosciences Information Service, Mar. 2006, Abstract.
Kuzirian et al., "Bryostatin Enhancement of Memory in Hermissenda", Biol. Bull. 210:201-214 (Jun. 2006).
Kuzirian et al., "Pavlovian Conditioning-Specific Increases of the Ca2+-and GTP-Binding Protein, Calexcitin in Identified Hermissenda Visual Cells", Journal of Neurocytology, 30:993-1008 (2001).

Lamberti et al., "Antideppressant-like effects of endogenous histamine and of two histamine H1 receptor agonists in the mouse forced swim test", British Journal of Pharmacology, 123(7): 1331-1336 (Jan. 1, 1998).
Lee et al., "Ubiquitination of Protein Kinase C-α and Degradation by the Proteasome," J. Biol. Chem., 271(35): 20973-27976 (Jun. 3, 1996).
Lenox et al., "Lithium and the Brain: A Psychopharmacological Strategy to a Molecular Basis for Manic Depressive Illness," Clin. Chem. 40(2):309-314 (1994).
Leontieva et al., "Identification of Two Distinct Pathways of Protein Kinase Ca Down-regulation in Intestinal Epthelial Cells", The Journal of Biological Chemistry, 279(7):5788-5801 (2004).
Li et al., "Endothelin Receptor Antagonist CPU0213 and Vitamin E Reverse Downregulation of FKBP12.6 and SERCA2a: A Role of Hyperphosphorylation of PKCε," European Journal of Pharmacology, 59:211-18 (2008).
Lieb et al., "Valproic Acid inhibits substance P-induced Activation of Protein Kinase C Epsilon and Expression of the Substance P Receptor," Journal of Neurochemistry, 86:69-76 (2003).
Lu et al., "Activation of Protein Kinase C Triggers Its Ubiquitination and Degradation," Molecular and Cellular Biology, 18(2): 839-345 (Feb. 1983).
Lyketsos, "Treating Depression in Alzheimer Disease, Efficacy and Safety of Sertraline Therapy, and the Benefits of Depression Reduction: The DIADS", Arch Gen Psychiatry, 2003, 60, pp. 737-746.
Maiorini et al., "Potential Novel Targets for Alzheimer Pharmacotherapy: I. Secretase," Journal of Clinical Pharmacy and Therapeutics, 27:169-183 (2002).
Manji et al. "Protein Kinase C Signaling in the Brain: Molecular Transduction of Mood Stabilization in the Treatment of Manic-Depressive Illness," Biol. Psychiatry 46(10)1328-1351 (1999).
Manji et al., "Post-receptor Signaling Pathways in the Pathophysiology and Treatment of Mood Disorders," Current Psychiatry Reports 2(6): 479-489 (2000).
Mannisto et al., "Beneficial Effects of Co-administration of Catechol-O-Methyltransferase Inhibitors and L-dihydroxyphenylalanine in Rat Models of Depression", European Journal of Pharmacology, 274:229-233 (1995).
Marshall et al., "Phase 1 Study of Prolonged Infusion Bryostatin-1 in Patients with Advanced Malignancies", Cancer Biology & Therapy 1:4, 409-416 (Jul./Aug. 2002).
Martin et al., "Role of vitamin E and C on neurodegenerative diseases and cognitive performance," Nutrition Review 60(11): 308-326 (2002).
Masliah et al., "Role of Amyloid Precursor Protein in the Mechanisms of Neurodegeneration in Alzheimer's Disease," Laboratory Investigation, 77(3)197-209 (1997).
Masliah, "Protein Kinase C Alteration Is an Early Biochemical Marker in Alzheimer's Disease," The Journal of Neuroscience, 11(9): 2759-2767 (1991).
Masson et al., "Neurotransmitter Transporters in the Central Nervous System," Pharmacological Reviews,51(3):439-464 (1999).
Matsui et al., "The Role of Growth Factors in the Activity of Pharmacological Differentiation Agents," Cell Growth and Differentiation, 13(6) (Jun. 2002), pp. 275-283.
McLoughlin et al., "Muscle Pains and Biochemical Changes Following Suxamethonium Administration After Six Pretreatment Regimens", Anaesthesia, 47:202-206 (1992).
McPhie et al., "Cell Specificity of Molecular Changes During Memory Storage", Journal of Neurochemistry, 60(2):646-651 (1993).
Mody et al., "Genome-wide expression profiles of the developing mouse hippocampus,", PNAS, 98(15):8862-8867 (Jul. 17, 2001).
Morishita et al., "Different Effect of Desipramine on Protein Kinase C in Platelets Between Bipolar and Major Depressive Disorders," Psychiatry and Clinical Neurosciences, 53:11-15 (1999).
Morshita et al., "Effects of Tricylic Antidepressants on Protein Kinase C Activity in Rabbit and Human Platelets in Vivo," Journal of Affective Disorders, 70:329-332 (2002).
Muscat et al., "Antidepressant-Like Effects of Dopamine Agonists in an Animal Model of Depression." Biol Psychiatry, 31: 937-946 (1992).

(56) References Cited

OTHER PUBLICATIONS

Nagata et al., "FR236924, a Newly Synthesized Derivataive of Linoleic Acid, Ameliorates Memory Deficits in Rats Intraventricularly Injected with Amyloid-Beta Peptide." Jpn. J. Physiol. 319: 53,Suppl. S261 (2003).
Nagata et al., "The Newly Synthesized Linoleic Acid Derivative CP-LA Ameliorates Memory Deficits in Animal Dmodels Treated with Amyloid-β Peptide and Scopolamine", Psychogeriatrics, 5:122-126 (2005).
Namba, Y. et al., "Apolipoprotein E Immunoreactivity in Cerebral Amyloid Deposits and Neurofibrillary Tangles in Alkzheimer's Disease and Kuru Plaque Amyloid in Creutzfeldt-Jakob Disease", Brain Research, 541(1): 163-166 (Feb. 8, 1991).
Nan et al., "Dual Function Glutamate-Related Ligands: Discovery of a Novel, Potent Inhibitor of Glutamate Carboxypeptidase II Possessing mGluR3 Agonist Activity," Journal of Medicinal Chemistry, 43(5):772-774 (2000).
Nelson et al., "Isolation of a G Protein That Is Modified by Learning and Reduces Potassium Currents in Hermissenda," Science, 247:1479-1483 (Mar. 23, 1990).
Nelson et al., "Specific High Molecular Weight mRNAs Induced by Associative Learning in Hermissenda", Proc. Nat. Acad. Sci. USA, 87:269-273 (Jan. 1990).
Nishizuka, Y., "Studies and prospectives of the protein kinase C family for cellular regulation", Cancer, 63(10): 1892-1903 (1989).
NME Digest, Drug News Perspect, 15(10): 666-674 (2002).
Office Action (Final) mailed Dec. 3, 2013, in U.S. Appl. No. 12/883,444.
Office Action (Restriction Requirement) mailed Aug. 10, 2010, in U.S. Appl. No. 11/802,723.
Office Action mailed Feb. 19, 2014, in U.S. Appl. No. 13/042,892.
Office Action mailed Jun. 26, 2013, in U.S. Appl. No. 12/833,444.
Office Action (Final) mailed Dec. 2, 2013, in U.S. Appl. No. 11/802,842.
Office Action (final) mailed Jun. 11, 2014 in U.S. Appl. No. 12/538,245.
Office Action (Final) mailed Jun. 2, 2014 in U.S. Appl. No. 12/068,742.
Office Action mailed Jan. 10, 2014, in U.S. Appl. No. 12/068,742.
Office Action mailed Jul. 16, 2013, in U.S. Appl. No. 11/802,842.
Office Action mailed May 22, 2013, in U.S. Appl. No. 13/561,770.
Office Action mailed Nov. 4, 2013, in U.S. Appl. No. 12/538,245.
Ohbayashi et al., "Structure and Expression of the mRNA Encoding a Novel Fibroblast Growth Factor, FGF-18," The Journal of Biological Chemistry, 273(29):18161-18164 (1998).
Olds et al., "Discrimination Learning Alters the Distribution of Protein Kinase C in the Hippocampus of Rats," The Journal of Neurosciences, 10(11):3707-3713 (Nov. 1990).
Olds et al., "Imaging of Memory-Specific Changes in the Distribution of Protein Kinase C in the Hippocampus", Science, 245:866-869 (Aug. 25, 1989).
Ortega et al., "Cognitive Function in Elderly People is Influenced by Vitamin E status." J. Nutrition, 132(7):2065-2068 (2002).
Pandey et al., "Protein Kinase C in Platelets of Depressed Patients," Biological Psychiatry, 44:909-911 (1998).
Pandey et al., "Protein Kinase C and Phospholipase C Activity and Expression of Their Specific Isozymes is Decreased and Expression of MARCKS is Increased in Platelets of Bipolar but Not in Unipolar Patients," Neuropschoparmacology, 26(2):216-228 (2002).
Partial European Search Report EP 08 01 0738, dated Oct. 6, 2009.
Partial European Search Report EP 12005992.8, dated Jan. 31, 2013, 8 pages.
Patella et al., "The Antineoplastic Bryostatins Affect Human Basophils and Mast Cells Differently," Blood, 85(5):1272-1281 (1995).
Pettit et al., "Antineoplastic Agents 224 Isolation and Structure of Neristatin 1," Journal of the American Chemical Society, 113(17):6693-6695 (1991).
PKC Lab, pp. 1-4, retrieved from: http://www.pkclab.org/PKC/PKCbiology/PKCbiology_PKC_activators.htm (2010).
Popoli et al., "Second Messenger-Regulated Protein Kinases in the Brain: Their Functional Role and the Action of Antidepressant Drugs," J. Neurochem.74(1):21-31 (2000).
Prendville et al., "A phase I study of intravenous bryostatin 1 in patients with advanced cancer", British J Cancer., 68(2): 418-424 (1993).
Prevostel et al., "Protein Kinase Cα Actively Downregulates Through Caveolae-Dependent Traffic to an Endosomal Compartment," Journal of Cell Science, 113:2575-2584 (2000).
Price, D.L. et al., "Alzheimer Disease and the Prion Disorders Amyloid .beta.-protein and Prion Protein Amyloidoses", Proceedings of the National Academy of Sciences of USA, 90(14): 6381-6384 (Jul. 15, 1993).
Protein Kinase C, pp. 1-6, 2010, retrieved from: http://en.wikipedia.org/wiki/Protein_kinase_C.
Quattrone et al., "Posttranscriptional Regulation of Gene Expression in Learning by the Neuronal ELAV-Like mRNA-Stabilizing Proteins", PNAS, 98(20): 11668-11673, (Sep. 25, 2001).
Rampello et al., "Dopamine and Depression: Therapeutic Implications CNS," Drugs, 13(1): 35-42 (Jan. 1, 2000).
Ricarelli et al., Vitamin E: Protective Role of a Janus Molecule. The FASEB Journal, 15:2314-2315 (2005).
Robner et al., "Short Communication: Protein Kinase Cα and β1 Isoforms are Regulators of α-Secretary Proteolytic Processing of Amyloid Precursor Protein in Vivo," European Journal of Neuroscience, 13:1644-1648 (2001).
Sanchez-Andres et al., "Voltage-clamp analysis of the effect of classical conditioning on the hippocampus", J Neurophysiol. 65(4): 796-807, 1991.
Sano et al., "A Controlled Trial of Selegiline, Alpha-Tocopherol, or Both as Treatment for Alzheimer's Disease", New England Journal of Medicine, 336(17): 1216-1222, Apr. 24, 1997.
Savage et al., "Turnover of Amyloid β-Protein in Mouse Brain and Acute Reduction of Its Level by Phorbol Ester," The Journal of Neuroscience, 18(5):1743-1752 (1998).
Scheuner et al., "Secreted Amyloid β-Protein Similar to that in the Senile Plaques of Alzheimer's Disease is Increased in Vivo by the Presenilin 1 and 2 and APP Mutations linked to Familial Alzheimer's Disease," Nature Medicine, 2(8): 864-870 (1996).
Schrenk et al., "Alterned Dendritic Development of Cerebellar Purkinje Cells in Slice Cultures from Protein Kinase Cgamma-deficient Mice," Neuroscience, 110(4):675-689 (2002).
Scioletti et al., "Memory Enhancement by Bryostain in Hermissenda", Biol. Bull., 207: p. 159 (Oct. 2004).
Selkoe, "Alzheimer's Disease: Genes, Proteins, and Therapy," Physiological Reviews, 81(2):741-766 (2001).
Selkoe, "Normal and Abnormal Biology of the β-Amyloid Precursor Protein," Annu. Re. Neurosci., 17:489-517 (1994).
Selkoe, "Translating Cell Biology into Therapeutic Advances in Alzheimer's Disease," Nature, 399(24):A23-A31 (1999).
Shelton, "Cellular Mechanisms in the Vulnerability to Depression and Response to Antidepressants," Depression, 23(4): 713-729 (Dec. 2000).
Shoulson, "Experimental Therapeutics of Neurodegenerative Disorders: Unmet Needs," Science, 282:1072-1074 (1998).
Sinha et al., "Purification and Cloning of Amyloid Precursor Protein β-Secretase from Human Brain," Nature, 402:537-540, (1999).
Skovronsky et al., Protein Kinase C-Dependent α-Secretase Competes with β-Secretase for Cleavage of Amyloid-β Precursor Protein in the Trans-Golgi Network, The Journal of Biological Chemistry, 275(4):2568-2575 (2000).
Small et al., "Alzheimer's Disease and the Amyloid β Protein: What is the Role of Amyloid?," Journal of Neurochemistry, 73(2):443:449 (1999).
Smith et al., "Inhibition of the proteasome converts bryostatin from an antagonist to an agonist of protein kinase C (PKC)," FASEB Journal, Fed. of American Soc. for Experimental Biology, US, vol. 11, No. 9, Jan. 1, 1997, p. A987.
St. George-Hyslop et al., "The genetic defect causing familial Alzheimer's disease maps on chromosome 21", Science, 235(4791): 885-890 (Feb. 1987).

(56) References Cited

OTHER PUBLICATIONS

Sun et al., "Carbonic Anhydrase Gating of Attention: Memory Therapy and Enhancement," TRENDS in Pharmacological Sciences, 23(2): 83-89 (Feb. 2002).
Sun et al., "Depressed or Demented: Common CNS Drug Targets?!", Current Drug Targets—CNS & Neurological Disorders 2002, 1, 575-592.
Sun et al., "Dual Effects of Bryostatin-1 on Spatial Memory and Depression", Eur. J. Pharmacol., vol. 512, pp. 43-51, 2005.
Sun et al., "Functional Switching of GABAergic Synapses by Ryanodine Receptor Activation," Proc. Nat'l. Acad. Sci USA, 97(22):12300-12305 (2000).
Sun et al., "Synergistic Effects of Chronic Bryostatin-1 and Alpha-tocopherol on Spatial Learning and Memory," Eur. J. Pharmacol., 584:328-337 (2008).
Supplemental Partial European Search Report for EP03742389 dated Sep. 12, 2007.
Supplementary European Search Report for PCT/US2003/07101 dated Aug. 6, 2008.
Supuran et al., Carbonic Anhydrase Activators. XV. A Kinetic Study of Interaction of Bovine Isozyme II with Pyrazoles, Bis- and Tris-azolyl-methanes:, Biol. Pharm. Bull., 19(11):1417-1422 (1996).
Suzuki et al., "Altered 5-HT-Induced Calcium Response in the Presence of Staurosporine in Blood Platelets from Bipolar Disorder Patients," Neuropsychopharmacology, 28:1210-1214 (2003).
Szallasi et al., "Differential Regulation of Protein Kinase C Isozymes by Cryostatin 1 and Phorbol 12-Myristate 13-Acetate in NIH 3T3 Fibroblasts," Journal of Biological Chemistry, 269(3):2118-2124 (1994).
Talk et al., "Neurophysiological Substrates of Context Conditioning in Hermissenda Suggest a Temporally Invariant Form of Activity-Dependent Neuronal Facilitation", Neurobiology of Learning and Memory, 72:95-117 (1999).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurolobiology of Disease, 3:159-168 (1996).
Tanzi et al., "Protease Inhibitor domain encoded by an amyloid protein precursor mRNA associated with Alzheimer's disease," Nature, 331:528-530 (1988).
Tenovuo, "Pharmacological Enhancement of Cognitive and Behavioral Deficits after Traumatic Brain Injury," Curr. Op. Neur., 19:528-533 (2006).
Tischmeyer et al., "Activation of Immediate Early Genes and Memory Formation", CMLS, Cell. Mol. Life Sci., 55:564-574 (1999).
Tsien et al., "The Essential Role of Hippocampal CA1 NMDA Receptor-Dependent Synaptic Plasticity in Spatial Memory," Cell, 87:1327-1338 (Dec. 27, 1996).
Turner et al., "Specificity of Memapsin 1 and Its Implications on the Design of Memapsin 2 (β-Secretase) Inhibitor Selectivity," Biochemistry, 41:8742-8746 (2002).
U.S. Department of Health and Human Services Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 6, 2005, Pharmacology and Toxicology, 30 pages.
Varterasian et al., "Phase II Trial of Bryostatin 1 in Patients with Relapsed Low-Grade Non-Hodgkin's Lymphoma and Chronic Lymphocytic Leukemia," Clinical Cancer Research, 6: 825-828, 2000.
Vassar et al., A-Generating Enzymes: Recent Advances in Band y-Secretase Research, Neuron, 27:419-422 (2000).
Vassar et al., "Secretase Cleavage of Alzheimer's Amyloid Precursor Protein by the Transmembrane Aspartic Protease BACE," Science, 286:735-741 (1999).

Vrontakis et al., "Current Drug Targets-CNS & Neurological Disorders. Glanain; A Biologically Active Peptide," 1(6):531-541 (2002).
Wang et al., "Attenuated Protein Kinase C Activity and Translocation in Alzheimer's Disease Brain," Neurobiology of Aging, 15(3):293-298 (1994).
Wang et al., "Flouxetine Depresses Glutamate Exocytosis in the Rat Cerebrocortical Nerve Terminals (Synaptosomes) via Inhibition of p/a Ca2+ Channels," Synapse 48:170-177 (2003).
Wang et al., "Increased Membrane-Associated Protein Kinase C Activity and Translocation in Blood Platelets from Bipolar Affective Disorder Patients," Journal of Psychiatric Research, 33:171-179 (1999).
Wang et al., "Neuroprotection Targets After Traumatic Brain Injury," Curr. Op. Neur., 19:514-519 (2006).
Webb et al., "Protein Kinase C Isoenzymes: A Review of Their Structure, Regulation and Role in Regulating Airways Smooth Muscle Tone and Mitogenesis," British Journal of Pharmacology, 130:1433-1452, 2000.
Weitman et al., "A Phase I Trial of Bryostatin-1 in Children with Refractory Solid Tumors: A Pediatric Oncology Group Study", Clinical Cancer Research, 5: 2344-2348, 1999.
Wender et al., "Function Oriented Synthesis: The Design, Synthesis, PCK Binding and Translocation Activity of a New Bryostatin Analog," 1 Curr. Drug Disc. Tech. 1 (2004).
Wender et al., "The Design, Computer Modeling, Solution Structure, and Biological Evaluation of Synthetic Analogs of Bryostatin I," Proc. Natl. Acad. Sci., 95: 6624-6629 (Jun. 1998).
Wender et al., "Total Synthesis and Initial Biological Evaluation of New B-Ring Modified Bryostatin Analogs," Organic Letters, 8(23): 5299-5302 (Oct. 2006).
Wender, "Role of the A-Ring of Bryostatin Analogues in PKkC Binding: Synthesis and Initial Biological Evaluation of New A-Ring Modified," Bryologs. Organic Letters, 7(10):1995-1998 (2005).
Wilkinson et al., "Research Communication: Isoenzyme specificity of bisindolylmaleimides, selective inhibitors of protein kinase C", Biochem. J. (1993) 294, 335-337.
Wiltfang et al., "Molecular Biology of Alzheimer's Dementia and Its Clinical Relevance to Early Diagnosis and New Therapeutic Strategies," Gerontology, 47:65-71 (2001).
Woolf et al., "Hippocampal Microtubule-associated Protein-2 Alterations with Contextual Memory", Brain Research, 821(1):241-249 (Mar. 6, 1999).
Xu et al., "Metabolism of Alzheimer β-Amyloid Precursor Protein; Regulation by Protein Kinase A in Intact Cells and in a Cell-Free System," Proc. Natl. Acad. Sci. USA, 93:4081-4084 (1996).
Yaguchi et al., "Effects of Cis-Unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamada, K. et al., "Protective Effects of Idenbenone and Alpha-tocopherol on Beta-amyloid-(1-42)-induced Learning and Memory Deficits in rats: Implication of Oxidative Stress in Beta-amyloid-induced Neurotoxicity in vivo", 11(1): 83-90 (Jan. 1999).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Yamanouchi et al., "Early Forms of Microtubule-associated Protein are Strongly Expressed in Cortical Dysplasia", Acta Neuropathol, 95:466-470 (1998).
Yildiz, "Phosphoinositide metabolism, lithium and manic depresive illness," Spectroscopy 16:307-316 (2002).
Zhang et al., "Citron Binds to PSD-95 at Glutamatergic Synapses on Inhibitory Neurons in the Hippocampus" The Journal of Neuroscience, 19(1):96-108 (Jan. 1, 1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).

(56) References Cited

OTHER PUBLICATIONS

Zhao et al., "Spatial learning induced changes in expression of the ryanodine type II receptor in the rat hippocampus," The FASEB Journal, 14:290-300 (Feb. 2000).
Zhen et al., "The p38 Mitogen-Activated Protein Kinase Is Involved in Associative Learning in Rabbits," The Journal of Neuroscience, 2(15):5513-5519 (Aug. 1, 2001).
Baltuch, G.H. et al., "Protein Kinase C Inhibitors Suppress Cell Growth in Established and Low-passage Glioma Cell Lines. A Comparison Between Staurosporine and Tamoxifen", Neurosurgery, Sep. 1993, vol. 33, No. 3, pp. 495-501.
Bhagavan, S. et al., "Restoration of TEA-Induced Calcium Responses in Fibroblasts from Alzheimer's Disease Patients by a PKC Activator," Neurobiology of Disease; Experimental Neurology, Part B., vol. 5, No. 3, Sep. 1998, pp. 177-187.
Blobe et al., "Regulation of protein kinase C and role in cancer biology," Cancer Metast. Rev. 1994; 13:411-431.
Extended European Search Report in 14001452.3 dated Jul. 4, 2014.
Extended European Search Report, for EP Application No. 14001303.8 dated Nov. 21, 2014.
Govoni et al., "Fibroblasts of Patients Affected by Down's Syndrome Oversecrete Amyloid Precursor Protein and are Hyporesponsive to Protein Kinase C Stimulation," Neurology, 46:1069-1075 (1996).
Hug et al., "Protein kinase C isoenzymes: divergence in signal transduction?" Biochem J. 1993;291:329-343.
Kuzirian et al., "Bryostatin Enhancement of Memory in Hermissenda," Biol. Bull. 210: 201-214 (Jun. 2006).
McKhann et al., "Clinical diagnosis of Alzheimer's disease: report of the NINCDS-ADRDA Work Group under the auspices of Department of Health and Human Services Task Force on Alzheimer's Disease", Neurology, vol. 34. No. 7, pp. 939-944, Jul. 1984.
Office Action mailed Nov. 17, 2014, in U.S. Appl. No. 12/883,444.
Office Action (Final) mailed Jun. 26, 2014 in U.S. Appl. No. 13/042,892.
Office Action (non-final) mailed Nov. 4, 2014, in co-pending U.S. Appl. No. 11/802,842.
Shimohama et al., "Assessment of Protein Kinase C Isozymes by Two-Site Enzyme Immunoassay in Human Brains and Changes in Alzheimer's Disease," Neurology, 43:1407-1413 (1993).
Yaguchi et al., "The CIS-Unsaturated Free Fatty Acid Derivative HEPBA Regulates $\alpha 7$ Nicotinic ACh receptor Trafficking, and Synaptic Plasticity Via a CAMKII Pathway," Dept. of Physiology, Hyogo College of Med., Hyogo, Japan, Bulletin of the Japanese Society for Neurochemistry, 2008, 47(2/3): 222.
Chochinov, "Depression in cancer patients", Lancet Oncology, 2:499-505 (2001).
Office Action (Final) mailed Jun. 9, 2015, in U.S. Appl. No. 11/802,842.
Office Action (final) mailed Jul. 13, 2015, in co-pending U.S. Appl. No. 12/883,444.
Office Action (Final) mailed Oct. 8, 2015, in U.S. Appl. No. 12/068,742.
Office Action mailed Feb. 13, 2015, in U.S. Appl. No. 13/660,567.
Office Action mailed Mar. 16, 2015, in U.S. Appl. No. 12/068,742.
Office Action mailed Sep. 21, 2015, in U.S. Appl. No. 13/042,892.
Lee et al., "Dephosphorylation of activated protein kinase C contributes to downregulation by bryostatin," Am. Physiological Soc. 1996, C304-C311.
Office Action (final) mailed Jan. 20, 2016, in U.S. Appl. No. 13/669,353.
Office Action (final) mailed May 5, 2016, U.S. Appl. No. 13/042,892.
Office Action (non-final) mailed May 10, 2016, U.S. Appl. No. 12/068,742.
Office Action mailed Feb. 1, 2016, U.S. Appl. No. 11/802,842.
Office Action mailed Jun. 1, 2016, in U.S. Appl. No. 14/196,455.

\* cited by examiner

METHODS FOR ALZHEIMER'S DISEASE TREATMENT AND COGNITIVE ENHANCEMENT

PRIORITY OF INVENTION

This is a continuation of application Ser. No. 10/933,536, filed Sep. 3, 2004, which is a divisional of U.S. application Ser. No. 10/167,491, filed on Jun. 13, 2002, now U.S. Pat. No. 6,825,229, and which claims priority to U.S. Provisional Application No. 60/362,080, filed Mar. 7, 2002, all of which are incorporated herein by reference.

BACKGROUND OF THE INVENTION (i) Field of the Invention

The present invention relates to the modulation of α-secretase and cognitive enhancement. The invention further relates to compounds for treatment of conditions associated with amyloid processing such as Alzheimer's Disease and compositions for the treatment of such conditions.

(ii) Background of the Invention

Various disorders and diseases exist which affect cognition. Cognition can be generally described as including at least three different components: attention, learning, and memory. Each of these components and their respective levels affect the overall level of a subject's cognitive ability. For instance, while Alzheimer's Disease patients suffer from a loss of overall cognition and thus deterioration of each of these characteristics, it is the loss of memory that is most often associated with the disease. In other diseases patients suffer from cognitive impairment that is more predominately associated with different characteristics of cognition. For instance Attention Deficit Hyperactivity Disorder (ADHD), focuses on the individual's ability to maintain an attentive state. Other conditions include general dementias associated with other neurological diseases, aging, and treatment of conditions that can cause deleterious effects on mental capacity, such as cancer treatments, stroke/ischemia, and mental retardation.

Cognition disorders create a variety of problems for today's society. Therefore, scientists have made efforts to develop cognitive enhancers or cognition activators. The cognition enhancers or activators that have been developed are generally classified to include nootropics, vasodilators, metabolic enhancers, psychostimulants, cholinergic agents, biogenic amine drugs, and neuropeptides. Vasodilators and metabolic enhancers (e.g. dihydroergotoxine) are mainly effective in the cognition disorders induced by cerebral vessel ligation-ischemia; however, they are ineffective in clinical use and with other types of cognition disorders. Of the developed cognition enhancers, typically only metabolic drugs are employed for clinical use, as others are still in the investigation stage. Of the nootropics for instance, piracetam activates the peripheral endocrine system, which is not appropriate for Alzheimer's disease due to the high concentration of steroids produced in patients while tacrine, a cholinergic agent, has a variety of side effects including vomiting, diarrhea, and hepatotoxicity.

Ways to improve the cognitive abilities of diseased individuals have been the subject of various studies. Recently the cognitive state related to Alzheimer's Disease and different ways to improve patient's memory have been the subject of various approaches and strategies. Unfortunately, these approaches and strategies only improve symptomatic and transient cognition in diseased individuals but have not addressed the progression of the disease. In the case of Alzheimer's Disease, efforts to improve cognition, typically through the cholinergic pathways or though other brain transmitter pathways, have been investigated. The primary approach relies on the inhibition of acetyl cholinesterase enzymes through drug therapy. Acetyl cholinesterase is a major brain enzyme and manipulating its levels can result in various changes to other neurological functions and cause side effects.

While these and other methods may improve cognition, at least transiently, they do not modify the disease progression, or address the cause of the disease. For instance, Alzheimer's Disease is typically associated with the formation of plaques through the accumulation of amyloid precursor protein. Attempts to illicit an immunological response through treatment against amyloid and plaque formation have been done in animal models, but have not been successfully extended to humans.

Furthermore, cholinesterase inhibitors only produce some symptomatic improvement for a short time and in only a fraction of the Alzheimer's Disease patients with mid to moderate symptoms and are thus only a useful treatment for a small portion of the overall patient population. Even more critical is that present efforts at improving cognition do not result in treatment of the disease condition, but are merely ameliorative of the symptoms. Current treatments do not modify the disease progression. These treatments have also included the use of a "vaccine" to treat the symptoms of Alzheimer's Disease patients which, while theoretically plausible and effective in mice tests, have been shown to cause severe adverse reactions in humans.

As a result, use of the cholinergic pathway for the treatment of cognitive impairment, particularly in Alzheimer's Disease, has proven to be inadequate. Additionally, the current treatments for cognitive improvement are limited to specific neurodegenerative diseases and have not proven effective in the treatment of other cognitive conditions.

Alzheimer's disease is associated with extensive loss of specific neuronal subpopulations in the brain with memory loss being the most universal symptom. (Katzman, R. (1986) New England Journal of Medicine 314:964). Alzheimer's disease is well characterized with regard to neuropathological changes. However, abnormalities have been reported in peripheral tissue supporting the possibility that Alzheimer's disease is a systemic disorder with pathology of the central nervous system being the most prominent. (Connolly, G., Fibroblast models of neurological disorders: fluorescence measurement studies, Review, TiPS Vol. 19, 171-77 (1998)). For a discussion of Alzheimer's disease links to a genetic origin and chromosomes 1, 14, and 21 see St. George-Hyslop, P. H., et al., Science 235:885 (1987); Tanzi, Rudolph et al., The Gene Defects Responsible for Familial Alzheimer's Disease, Review, Neurobiology of Disease 3, 159-168 (1996); Hardy, J., Molecular genetics of Alzheimer's disease, Acta Neurol Scand: Supplement 165: 13-17 (1996).

While cellular changes leading to neuronal loss and the underlying etiology of the disease remain under investigation the importance of APP metabolism is well established. The two proteins most consistently identified in the brains of patients with Alzheimer's disease to play a role in the physiology or pathophysiology of brain are β-amyloid and tau. (See Selkoe, D., Alzheimer's Disease: Genes, Proteins, and Therapy, Physiological Reviews, Vol. 81, No. 2, 2001). A discussion of the defects in β-amyloid protein metabolism and abnormal calcium homeostasis and/or calcium activated kinases. (Etcheberrigaray et al., Calcium responses are altered in fibroblasts from Alzheimer's patients and pre-symptomatic PS1 carriers: a potential tool for early diagnosis, Alzheimer's Reports, Vol. 3, Nos. 5 & 6, pp. 305-312 (2000); Webb et al., Protein kinase C isozymes: a review of their structure, regulation and role in regulating airways smooth muscle tone and mitogenesis, British Journal of Pharmacology, 130, pp 1433-52 (2000)).

Further with regard to normal and abnormal memory both $K^+$ and $Ca^{2+}$ channels have been demonstrated to play key roles in memory storage and recall. For instance, potassium channels have been found to change during memory storage. (Etcheberrigaray, R., et al. (1992) Proceeding of the National Academy of Science 89:7184; Sanchez-Andres, J. V. and Alkon, D. L. (1991) Journal of Neurobiology 65:796; Collin, C., et al. (1988) Biophysics Journal 55:955; Alkon, D. L., et al. (1985) Behavioral and Neural Biology 44:278; Alkon, D. L. (1984) Science 226:1037). This observation, coupled with the almost universal symptom of memory loss in Alzheimer's patients, led to the investigation of potassium channel function as a possible site of Alzheimer's disease pathology and the effect of PKC modulation on cognition.

PKC was identified as one of the largest gene families of non-receptor serine-threonine protein kinases. Since the discovery of PKC in the early eighties by Nishizuka and coworkers (Kikkawa et al., *J. Biol. Chem.*, 257, 13341 (1982), and its identification as a major receptor for phorbol esters (Ashendel et al., *Cancer Res.*, 43, 4333 (1983)), a multitude of physiological signaling mechanisms have been ascribed to this enzyme. The intense interest in PKC stems from its unique ability to be activated in vitro by calcium and diacylglycerol (and its phorbol ester mimetics), an effector whose formation is coupled to phospholipid turnover by the action of growth and differentiation factors.

The PKC gene family consists presently of 11 genes which are divided into four subgroups: 1) classical PKCα, $\beta_1$, $\beta_2$ ($\beta_1$ and $\beta_2$ are alternatively spliced forms of the same gene) and γ, 2) novel PKCδ, ε, η and θ, 3) atypical PKCξ, λ, η and ι and 4) PKCμ. PKCμ resembles the novel PKC isoforms but differs by having a putative transmembrane domain (reviewed by Blohe et al., *Cancer Metast. Rev.*, 13, 411 (1994); Ilug et al., *Biochem j.*, 291, 329 (1993); Kikkawa et al., *Ann. Rev. Biochem.* 58, 31 (1989)). The α, $\beta_1$, $\beta_2$, and γ isoforms are $Ca^{2+}$, phospholipid and diacylglycerol-dependent and represent the classical isoforms of PKC, whereas the other isoforms are activated by phospholipid and diacylglycerol but are not dependent on $Ca^{2+}$. All isoforms encompass 5 variable (V1-V5) regions, and the α, β, γ isoforms contain four (C1-C4) structural domains which are highly conserved. All isoforms except PKCα, β and γ lack the C2 domain, and the λ, η and isoforms also lack nine of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme (House et al., *Science*, 238, 1726 (1987)).

Because of these structural features, diverse PKC isoforms are thought to have highly specialized roles in signal transduction in response to physiological stimuli (Nishizuka, *Cancer*, 10, 1892 (1989)), as well as in neoplastic transformation and differentiation (Glazer, *Protein Kinase C*, J. F. Kuo, ed., Oxford U. Press (1994) at pages 171-198). For a discussion of known PKC modulators see PCT/US97/08141, U.S. Pat. Nos. 5,652,232; 6,043,270; 6,080,784; 5,891,906; 5,962,498; 5,955,501; 5,891,870 and 5,962,504.

In view of the central role that PKC plays in signal transduction, PKC has proven to be an exciting target for the modulation of APP processing. It is well established that PKC plays a role in APP processing. Phorbol esters for instance have been shown to significantly increase the relative amount of non-amyloidogenic soluble APP (sAPP) secreted through PKC activation. Activation of PKC by phorbol ester does not appear to result in a direct phosphorylation of the APP molecule, however. Irrespective of the precise site of action, phorbol-induced PKC activation results in an enhanced or favored α-secretase, non-amyloidogenic pathway. Therefore PKC activation is an attractive approach for influencing the production of non-deleterious sAPP and even producing beneficial sAPP and at the same time reduce the relative amount of Aβ peptides. Phorbol esters, however, are not suitable compounds for eventual drug development because of their tumor promotion activity. (Ibarreta, et al., Benzolactam (BL) enhances sAPP secretion in fibroblasts and in PC12 cells, NeuroReport, Vol. 10, No. 5&6, pp 1035-40 (1999)).

There is increasing evidence that the individual PKC isozymes play different, sometimes opposing, roles in biological processes, providing two directions for pharmacological exploitation. One is the design of specific (preferably, isozyme specific) inhibitors of PKC. This approach is complicated by the fact that the catalytic domain is not the domain primarily responsible for the isotype specificity of PKC. The other approach is to develop isozyme-selective, regulatory site-directed PKC activators. These may provide a way to override the effect of other signal transduction pathways with opposite biological effects. Alternatively, by inducing down-regulation of PKC after acute activation, PKC activators may cause long term antagonism. Bryostatin is currently in clinical trials as an anti-cancer agent. The bryostatins are known to bind to the regulatory domain of PKC and to activate the enzyme. Bryostatin is an example of isozyme-selective activators of PKC. Compounds in addition to bryostatins have been found to modulate PKC. (see for example WO 97/43268)

There still exists a need for the development of methods for the treatment for improved overall cognition, either through a specific characteristic of cognitive ability or general cognition. There also still exists a need for the development of methods for the improvement of cognitive enhancement whether or not it is related to specific disease state or cognitive disorder. The methods and compositions of the present invention fulfill these needs and will greatly improve the clinical treatment for Alzheimer's disease and other neurodegenerative diseases, as well as, provide for improved cognitive enhancement. The methods and compositions also provide treatment and/or enhancement of the cognitive state through the modulation of α-secretase.

SUMMARY OF THE INVENTION

The invention relates to compounds, compositions, and methods for the treatment of conditions associated with enhancement/improvement of cognitive ability. In a preferred embodiment, the present invention further relates to compounds, compositions and methods for the treatment of conditions associated with amyloid processing, such as Alzheimer's Disease, which provides for improved/enhanced cognitive ability in the subject treated. In particular the compounds and compositions of the present invention are selected from macrocyclic lactones (i.e. bryostatin class and neristatin class).

In another aspect the invention relates to macrocyclic lactone compounds, compositions and methods that modulate α-secretase activity. Of particular interest are the bryostatin and neristatin class compounds, and of further interest is bryostatin-1.

Another aspect of the invention relates to the bryostatin and neristatin class compounds, as a PKC activator, to alter conditions associated with amyloid processing in order to enhance the α-secretase pathway to generate soluble α-amyloid precursor protein (αAPP) so as to prevent β-amyloid aggregation and improve/enhance cognitive ability. Such activation, for example, can be employed in the treatment of Alzheimer's Disease. Of particular interest is bryostatin-1.

In another aspect, the invention relates to a method for treating plaque formation, such as that associated with Alzheimer's Disease, and improving/enhancing the cognitive state of the subject comprising administering to the subject an effective amount of a macrocyclic lactone to activate PKC. In a preferred embodiment, the PKC activator is of the bryostatin or neristatin class of compounds. In a more preferred embodiment the compound is bryostatin-1.

Another aspect of the invention relates to a composition for treating plaque formation and improving/enhancing cognitive ability comprising: (i) a macrocyclic lactone in an amount effective to elevate soluble β-amyloid, generate soluble αAPP and prevent β-amyloid aggregation; and (ii) a pharmaceutically effective carrier. In a preferred embodiment the composition is used to improve/enhance cognitive ability associated with Alzheimer's Disease. The macrocyclic lactone is preferably selected from the bryostatin or neristatin class compounds, particularly bryostatin-1.

In one embodiment of the invention the activation of PKC isoenzymes results in improved cognitive abilities. In one embodiment the improved cognitive ability is memory. In another embodiment the improved cognitive ability is learning. In another embodiment the improved cognitive ability is attention. In another embodiment PKC's isoenzymes are activated by a macrocyclic lactone (i.e. bryostatin class and neristatin class). In particular, bryostatin-1 through 18 and neristatin is used to activate the PKC isoenzyme. In a preferred embodiment bryostatin-1 is used.

In another aspect, the invention comprises a composition of a PKC isoenzyme activator administered in an amount effective to improve cognitive abilities. In a preferred embodiment the PKC isoenzyme activator is selected from macrocyclic lactones (i.e. bryostatin class and neristatin class). In a preferred embodiment the amount of PKC activator administered is in an amount effective to increase the production of sAPP. In a more preferred embodiment the amount of composition administered does not cause myalgia.

In a preferred embodiment the PKC isoenzymes are activated in subjects, which are suffering or have suffered from neurological diseases, strokes or hypoxia. In a more preferred embodiment the PKC isoenzyme is activated in Alzheimer's Disease subjects or models.

In another embodiment of the invention the PKC activation results in the modulation of amyloid precursor protein metabolism. Further the modulation by the PKC activation results in an increase in the alpha secretase pathway. The alpha secretase pathway results in non-toxic, non-amyloidogenic fragments related to cognitive impairment. As a result the cognitive condition of the subject improves. In another embodiment of the invention the PKC activation reduces the amyloidogenic and toxic fragments Abeta 40 and Ab42.

Another embodiment of the invention is a method of improving cognitive ability through the activation of PKC isoenzymes. In another embodiment of the invention the PKC activation occurs in "normal" subjects. In another embodiment of the invention the PKC activation occurs in subjects suffering from a disease, deteriorating cognitive faculties, or malfunctioning cognition. In a preferred embodiment the method is a method for treating Alzheimer's Disease.

In another embodiment of the invention the modulation of PKC is through the use of a non-tumor promoting agent resulting in improved cognitive abilities. In a preferred embodiment the PKC activator is selected from bryostatin-1 through bryostatin-18 and neristatin. In a more preferred embodiment bryostatin-1 is used. In another embodiment bryostatin-1 is used in combination with a non-bryostatin class compound to improve cognitive ability and reduce side effects.

In another embodiment of the invention, the modulation of PKC through macrocyclic lactones (i.e. bryostatin class and neristatin class) is used in vitro for the testing of conditions associated with Alzheimer's Disease. The in vitro use may include for example, the testing of fibroblast cells, blood cells, or the monitoring of ion channel conductance in cellular models.

In a preferred embodiment of the invention the compounds and compositions are administered through oral and/or injectable forms including intravenously and intraventricularly.

The present invention therefore provides a method of treating impaired memory or a learning disorder in a subject, the method comprising administering thereto a therapeutically effective amount of one of the present compounds. The present compounds can thus be used in the therapeutic treatment of clinical conditions in which memory defects or impaired learning occur. In this way memory and learning can be improved. The condition of the subject can thereby be improved.

The compositions and methods have utility in treating clinical conditions and disorders in which impaired memory or a learning disorder occurs, either as a central feature or as an associated symptom. Examples of such conditions which the present compounds can be used to treat include Alzheimer's disease, multi-infarct dementia and the Lewy-body variant of Alzheimer's disease with or without association with Parkinson's disease; Creutzfeld-Jakob disease and Korsakow's disorder.

The compositions and methods can also be used to treat impaired memory or learning which is age-associated, is consequent upon electro-convulsive therapy or which is the result of brain damage caused, for example, by stroke, an anesthetic accident, head trauma, hypoglycemia, carbon monoxide poisoning, lithium intoxication or a vitamin deficiency.

The compounds have the added advantage of being non-tumor promoting and already being involved in phase II clinical trials.

The invention relates to a pharmaceutical composition for enhancing cognition, preventing and/or treating cognition disorders. More particularly, it relates to the pharmaceutical composition comprising macrocyclic lactones (i.e. bryostatin class and neristatin class) and their derivatives as the active ingredient for enhancing cognition, preventing and/or treating cognition disorders.

It is therefore a primary object of the invention to provide pharmaceutical compositions for enhancing cognition, preventing and/or treating cognition disorders. The pharmaceutical composition comprises macrocyclic lactones, particularly the bryostatin and neristatin class, or a pharmaceutically acceptable salt or derivative thereof, and a pharmaceutically acceptable carrier or excipient.

The pharmaceutical composition according to the invention is useful in the enhancement of cognition, prophylaxis and/or treatment of cognition disorders, wherein cognition disorders include, but are not limited to, disorders of learning acquisition, memory consolidation, and retrieval, as described herein.

The invention concerns a method for the treatment of amyloidosis associated with neurological diseases, including Alzheimer's disease by administering to a patient an effective amount of at least one agent that modulates or affects the phosphorylation of proteins in mammalian cells.

The invention also provides a method for treating Alzheimer's disease comprising administering to a patient an effective amount of a macrocyclic lactone (i.e. bryostatin class and neristatin class).

In another embodiment the bryostatin or neristatin class compounds may be used in the above methods in combination with different phorbol esters to prevent or reduce tumorogenetic response in the subject.

BRIEF DESCRIPTION OF THE DRAWINGS

FIG. 5($b$) illustrates the amount of time treated rats spent swimming in the different quadrants.

FIG. 5($c$) illustrates the different between the amount of time the treated rats spent in target quadrant compared to control rats.

DETAILED DESCRIPTION OF THE PREFERRED EMBODIMENTS

Figure 1:
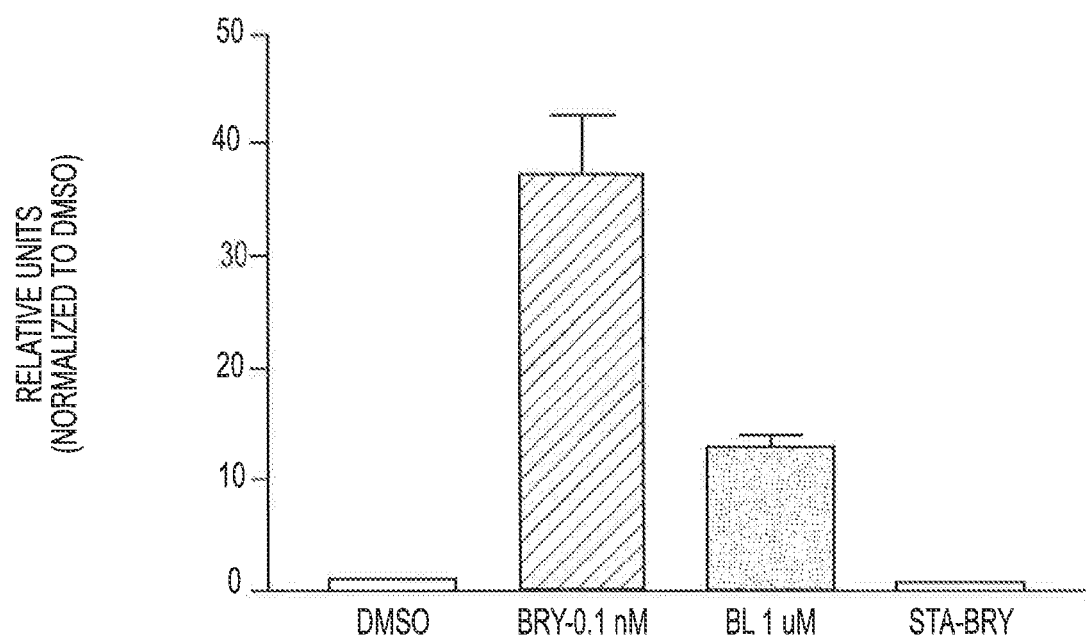
FIG. 1 illustrates the effect of different PKC inhibitors on sAPPα secretion with Bryostatin-1 showing greater efficacy at lower concentrations than controls and Benzolactam.

Memory loss and impaired learning ability are features of a range of clinical conditions. For instance, loss of memory is the most common symptom of dementia states including Alzheimer's disease. Memory defects also occur with other kinds of dementia such as multi-infarct dementia (MID), a senile dementia caused by cerebrovascular deficiency, and the Lewy-body variant of Alzheimer's disease with or without association with Parkinson's disease, or Creutzfeld-Jakob disease. Loss of memory is a common feature of brain-damaged patients. Brain damage may occur, for example, after a classical stroke or as a result of an anesthetic accident, head trauma, hypoglycemia, carbon monoxide poisoning, lithium intoxication, vitamin (B1, thiamine and B12) deficiency, or excessive alcohol use or Korsakow's disorder. Memory impairment may furthermore be age-associated; the ability to recall information such as names, places and words seems to decrease with increasing age. Transient memory loss may also occur in patients, suffering from a major depressive disorder, after electro-convulsive therapy (ECT). Alzheimer's disease is in fact the most important clinical entity responsible for progressive dementia in ageing populations, whereas hypoxia/stroke is responsible for significant memory defects not related to neurological disorders.

Individuals with Alzheimer's disease are characterized by progressive memory impairments, loss of language and visuospatial skills and behavior deficits (McKhann et al., 1986, Neurology, 34:939-944). The cognitive impairment of individuals with Alzheimer's disease is the result of degeneration of neuronal cells located in the cerebral cortex, hippocampus, basal forebrain and other brain regions. Histologic analyses of Alzheimer's disease brains obtained at autopsy demonstrated the presence of neurofibrillary tangles (NFT) in perikarya and axons of degenerating neurons, extracellular neuritic (senile) plaques, and amyloid plaques inside and around some blood vessels of affected brain regions. Neurofibrillary tangles are abnormal filamentous structures containing fibers (about 10 nm in diameter) that are paired in a helical fashion, therefore also called paired helical filaments. Neuritic plaques are located at degenerating nerve terminals (both axonal and dendritic), and contain a core compound of amyloid protein fibers. In summary, Alzheimer's disease is characterized by certain neuropathological features including intracellular neurofibrillary tangles, primarily composed of cytoskeletal proteins, and extracellular parenchymal and cerebrovascular amyloid. Further, there are now methods in the art for distinguishing between Alzheimer's patients, normal aged people, and people suffering from other neurodegenerative diseases, such as Parkinson's, Huntington's chorea, Wernicke-Korsakoff or schizophrenia further described for instance in U.S. Pat. No. 5,580,748 and U.S. Pat. No. 6,080,582.

Alzheimer's disease (AD) is a brain disorder characterized by altered protein catabolism. Altered protein phosphorylation has been implicated in the formation of the intracellular neurofibrillary tangles found in Alzheimer's disease. A role for protein phosphorylation in the catabolism of the amyloid precursor protein (APP), from which is derived the major component of amyloid plaques found in AD, has also been investigated. A central feature of the pathology of Alzheimer's disease is the deposition of amyloid protein within plaques.

The processing of the amyloid precursor protein (APP) determines the production of fragments that later aggregate forming the amyloid deposits characteristic of Alzheimer's disease (AD), known as senile or AD plaques. Thus, APP processing is an early and key pathophysiological event in AD.

Three alternative APP processing pathways have been identified. The previously termed "normal" processing involves the participation of an enzyme that cleaves APP within the Aβ sequence at residue Lys16 (or between Lys16 and Leu17; APP770 nomenclature), resulting in non-amyloidogenic fragments: a large N-terminus ectodomain and a small 9 kDa membrane bound fragment. This enzyme, yet to be fully identified, is known as α-secretase. Two additional secretases participate in APP processing. One alternative pathway involves the cleavage of APP outside the Aβ domain, between Met671 and Asp672 (by β-secretase) and the participation of the endosomal-lysomal system. An additional cleavage site occurs at the carboxyl-terminal end of the Aβ portion, within the plasma membrane after amino acid 39 of the Aβ peptide. The secretase (γ) action produces an extracellular amino acid terminal that contains the entire Aβ sequence and a cell-associated fragment of ~6 kDa. Thus, processing by β and γ secretases generate potential amyloidogenic fragments since they contain the complete Aβ sequence. Several lines of evidence have shown that all alternative pathways occur in a given system and that soluble Aβ may be a "normal product." However, there is also evidence that the amount of circulating Aβ in CSF and plasma is elevated in patients carrying the "Swedish" mutation. Moreover, cultured cells transfected with this mutation or the $APP_{717}$ mutation, secrete larger amounts of Aβ. More recently, carriers of other APP mutations and PS1 and PS2 mutations have been shown to secrete elevated amounts of a particular form, long (42-43 amino acids) Aβ.

Therefore, although all alternative pathways may take place normally, an imbalance favoring amyloidogenic processing occurs in familial and perhaps sporadic AD. These enhanced amyloidogenic pathways ultimately lead to fibril and plaque formation in the brains of AD patients. Thus, intervention to favor the non-amyloidogenic, α-secretase pathway effectively shifts the balance of APP processing towards a presumably non-pathogenic process that increases the relative amount of sAPP compared with the potentially toxic Aβ peptides.

The PKC isoenzymes provides a critical, specific and rate limiting molecular target through which a unique correlation of biochemical, biophysical, and behavioral efficacy can be demonstrated and applied to subjects to improve cognitive ability.

The present inventors have studied bryostatins as activators of protein kinase (PKC). Alterations in PKC, as well alterations in calcium regulation and potassium ($K^+$) channels are included among alterations in fibroblasts in Alzheimer's disease (AD) patients. PKC activation has been shown to restore normal $K^+$ channel function, as measured by TEA-induced $[Ca^{2+}]$ elevations. Further patch-clamp data substantiates the effect of PKC activators on restoration of 113 pS $K^+$ channel activity. Thus PKC activator-based restoration of $K^+$ channels has been established as an approach to the investigation of AD pathophysiology, and provides a useful model for AD therapeutics. (See pending application Ser. No. 09/652,656 herein incorporated in its entirety.)

The use of peripheral tissues from Alzheimer's disease (AD) patients and animal neuronal cells permitted the identification of a number of cellular/molecular alterations reflecting comparable processes in the AD brain and thus, of pathophysiological relevance (Baker et al., 1988; Scott, 1993; Huang, 1994; Scheuner et al., 1996; Etcheberrigaray & Alkon, 1997; Gasparini et al., 1997). Alteration of potassium channel function has been identified in fibroblasts (Etcheberrigaray et al., 1993) and in blood cells (Bondy et al., 1996) obtained from AD patients. In addition, it was shown that β-amyloid, widely accepted as a major player in AD pathophysiology (Gandy & Greengard, 1994; Selkoe, 1994; Yankner, 1996), was capable of inducing an AD-like $K^+$ channel alteration in control fibroblasts (Etcheberrigaray et al., 1994). Similar or comparable effects of β-amyloid on $K^+$ channels have been reported in neurons from laboratory animals (Good et al., 1996; also for a review see Fraser et al., 1997). An earlier observation of hippocampal alterations of apamin-sensitive $K^+$ channels in AD brains (as measured by apamin binding) provides additional support for the suggestion that $K^+$ channels may be pathophysiologically relevant in AD (Ikeda et al., 1991). Furthermore, protein kinase C (PKC) exhibits parallel changes in peripheral and brain tissues of AD patients. The levels and/or activity of this enzyme(s) were introduced in brains and fibroblasts from AD patients (Cole et al., 1988; Van Huynh et al., 1989; Govoni et al., 1993; Wang et al., 1994). Studies using immunoblotting analyses have revealed that of the various PKC isozymes, primarily the α isoform was significantly reduced in fibroblasts (Govoni et al., 1996), while both α and β isoforms are reduced in brains of AD patients (Shimohama et al., 1993; Masliah et al., 1990). These brain PKC alterations might be an early event in the disease process (Masliah et at, 1991). It is also interesting to note that PKC activation appears to favor nonamyloidogenic processing of the amyloid precursor protein, APP (Buxbaum et al., 1990; Gillespie et al., 1992; Selkoe, 1994; Gandy & Greengard, 1994; Bergamashi et al., 1995; Desdouits et al., 1996; Efhimiopoulus et al., 1996). Thus, both PKC and $K^+$ channel alterations coexist in AD, with peripheral and brain expression in AD.

The link between PKC and $K^+$ channel alterations has been investigated because PKC is known to regulate ion channels, including $K^+$ channels and that a defective PKC leads to defective $K^+$ channels. This is important not only for the modulation of APP, but also for the role PKC and $K^+$ channels play in memory establishment and recall. (e.g., see Alkon et al., 1988; Covarrubias et al., 1994; Hu et al., 1996) AD fibroblasts have been used to demonstrate both $K^+$ channels and PKC defects (Etcheberrigaray et al., 1993; Govoni et al., 1993, 1996). Studies also show, fibroblasts with known dysfunctional $K^+$ channels treated with PKC activators restore channel activity as monitored by the presence/absence of TEA-induced calcium elevations. Further, assays based on tetraethylammonium chloride (TEA)-induced $[Ca^{2+}]$ elevation have been used to show functional 113 pS $K^+$ channels that are susceptible to TEA blockade (Etcheberrigaray et al., 1993, 1994; Hirashima et al., 1996). Thus, TEA-induced $[Ca^{2+}]$ elevations and $K^+$ channel activity observed in fibroblasts from control individuals are virtually absent in fibroblasts from AD patients (Etcheberrigaray et al., 1993; Hirashima et al., 1996). These studies demonstrate that the use of PKC activators can restore the responsiveness of AD fibroblast cell lines to the TEA challenge. Further, immunoblot evidence from these studies demonstrate that this restoration is related to a preferential participation of the α isoform.

The present inventors have also observed that activation of protein kinase C favors the α-secretase processing of the Alzheimer's disease (AD) amyloid precursor protein (APP), resulting in the generation of non-amyloidogenic soluble APP (sAPP). Consequently, the relative secretion of amyloidogenic $A_{1-40}$ and $A_{1-42(3)}$ is reduced. This is particularly relevant since fibroblasts and other cells expressing APP and presenilin AD mutations secrete increased amounts of total Aβ and/or increased ratios of $A_{1-43(3)}/A_{1-40}$. Interestingly, PKC defects have been found in AD brain (α and β isoforms) and in fibroblasts (α-isoform) from AD patients.

Studies have shown that other PKC activators (i.e. benzolactam) with improved selectivity for the α, β, and γ isoforms enhance sAPP secretion over basal levels. The sAPP secretion in benzolactam-treated AD cells was also slightly higher compared to control benzolactam-treated fibroblasts, which only showed significant increases of sAPP secretion after treatment with 10 μM BL. It was further reported that staurosporine (a PKC inhibitor) eliminated the effects of benzolactam in both control and AD fibroblasts while related compounds also cause a ~3-fold sAPP secretion in PC12 cells. The present inventors have found that the use of bryostatin as a PKC activators to favor non-amyloidogenic APP processing is of particular therapeutic value since it is non-tumor promoting and already in stage II clinical trials.

Memories are thought to be a result of lasting synaptic modification in the brain structures related to information processing. Synapses are considered a critical site at final targets through which memory-related events realize their functional expression, whether the events involve changed gene expression and protein translation, altered kinase activities, or modified signaling cascades. A few proteins have been implicated in associative memory including $Ca^{2+}$/calmodulin II kinases, protein kinase C, calexcitin, a 22-kDa learning-associated $Ca^{2+}$ binding protein, and type II ryanodine receptors. The modulation of PKC through the administration of macrocyclic lactones provides a mechanism to effect synaptic modification.

The area of memory and learning impairment is rich in animal models that are able to demonstrate different features of memory and learning processes. (See, for example, Hollister, L. E., 1990, Pharmacopsychiat., 23, (Suppl II) 33-36). The available animal models of memory loss and impaired learning involve measuring the ability of animals to remember a discrete event. These tests include the Morris Water Maze and the passive avoidance procedure. In the Morris Water Maze, animals are allowed to swim in a tank divided into four quadrants, only one of which has a safety platform beneath the water. The platform is removed and the animals are tested for how long they search the correct quadrant verse the incorrect quadrants. In the passive avoidance procedure the animal remembers the distinctive environment in which a mild electric shock is delivered and avoids it on a second occasion. A variant of the passive avoidance procedure makes use of a rodent's preference for dark enclosed environments over light open ones. Further discussion can be found in Crawley, J. N., 1981, Pharmacol. Biochem. Behav., 15, 695-699; Costall, B. et al, 1987, Neuropharmacol., 26, 195-200; Costall, B. et al, 1989, Pharmacol. Biochem. Behav., 32, 777-785; Barnes, J. M. et al, 1989, Br. J. Pharmacol., 98 (Suppl) 693P; Barnes, J. M. et al, 1990, Pharmacol. Biochem. Behav., 35, 955-962.

The use of the word, "normal" is meant to include individuals who have not been diagnosis with or currently display diminished or otherwise impaired cognitive function. The different cognitive abilities may be tested and evaluated through known means well established in the art, including but not limited to tests from basic motor-spatial skills to more complex memory recall testing. Non-limiting examples of tests used for cognitive ability for non-primates include the Morris Water Maze, Radial Maze, T Maze, Eye Blink Conditioning, Delayed Recall, and Cued Recall while for primate subjects test may include Eye Blink, Delayed Recall, Cued Recall, Face Recognition, Minimental, and ADAS-Cog. Many of these tests are typically used in the mental state assessment for patients suffering from AD. Similarly, the evaluation for animal models for similar purposes with well describe in the literature.

Figure 2:
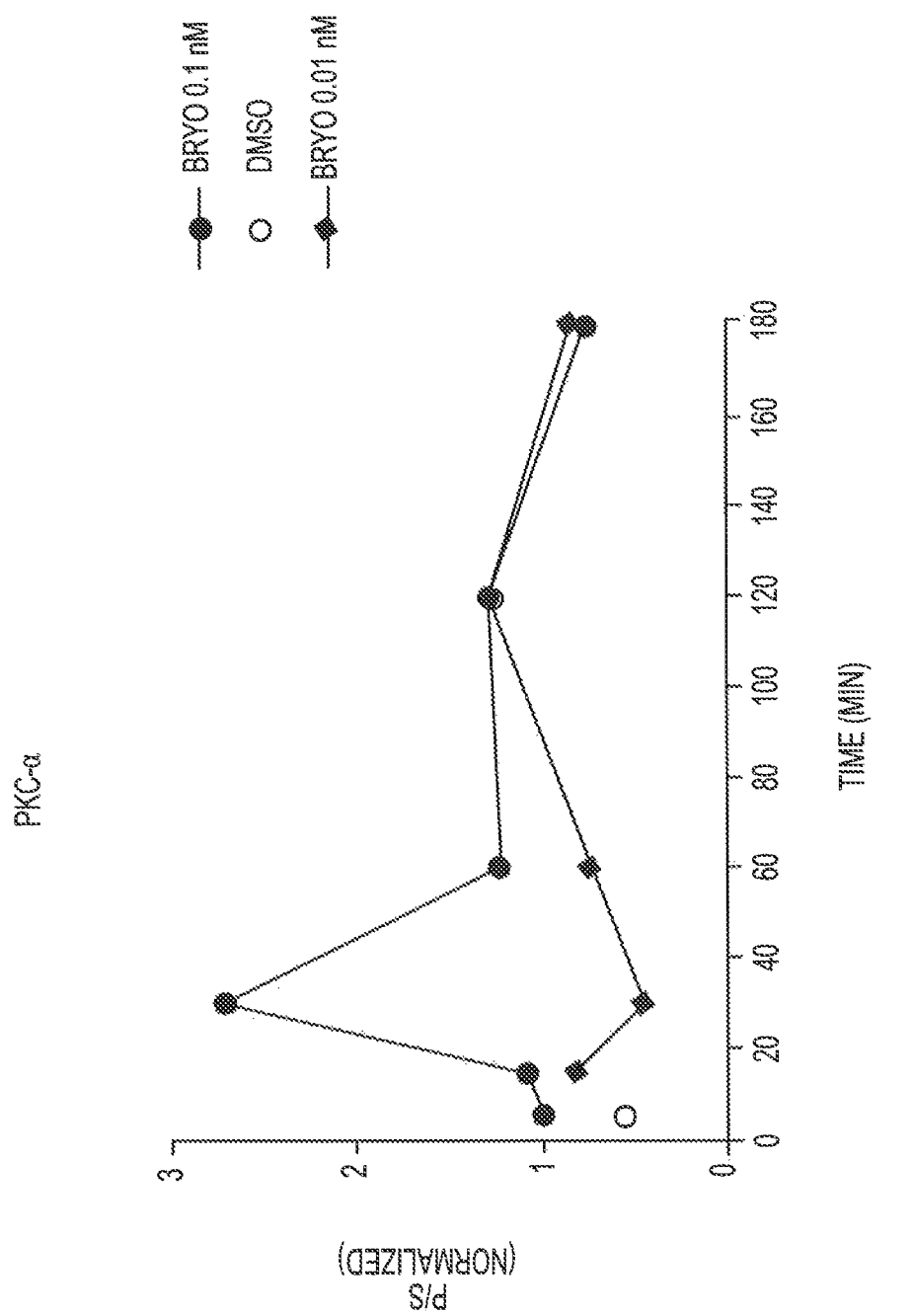
FIG. 2 illustrates the effect of different concentrations of Bryostatin-1 on the PKCα isozyme.
Figure 3:
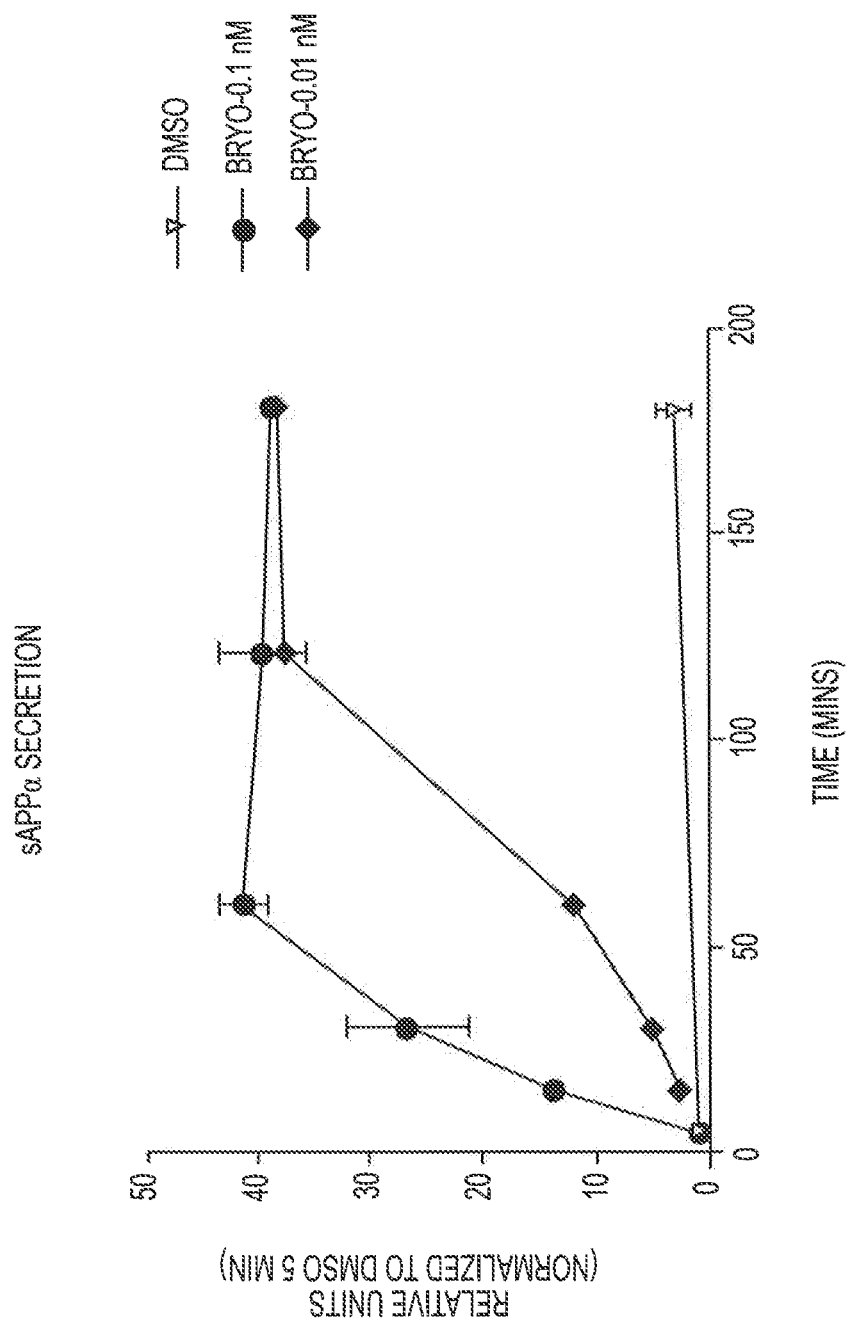
FIG. 3 illustrates the effect of different concentrations of Bryostatin-1 on sAPPα secretion.

Of particular interest are macrocyclic lactones (i.e. bryostatin class and neristatin class) that act to stimulate PKC. Of the bryostatin class compounds, bryostatin-1 has been shown to activate PKC and proven to be devoid of tumor promotion activity. Bryostatin-1, as a PKC activator, is also particularly useful since the dose response curve of bryostatin-1 is biphasic. Additionally, bryostatin-1 demonstrates differential regulation of PKC isozymes, including PKCα, PKCδ, and PKCϵ. Bryostatin-1 has undergone toxicity and safety studies in animals and humans and is actively being investigated as an anti-cancer agent. Bryostatin-1's use in the studies has determined that the main adverse reaction in humans is myalgia, limiting the maximum dose to 40 $mg/m^2$. The present invention has utilized concentrations of 0.1 nM of bryostatin-1 to cause a dramatic increase of sAPP secretion. Bryostatin-1 has been compared to a vehicle alone and to another PKC activator, benzolactam (BL), used at a concentration 10,000 times higher. Also bryostatin used at 0.01 nM still proved effective to increase sAPP secretion. (See FIG. 1). PKC translocation shows that a measure of activation is maximal at 30 min, followed by a partial decline, which remains higher than basal translocation levels up to six hours. (see FIGS. 2,3, & 7). The use of the PKC inhibitor staurosporin completely prevents the effect of bryostatin on sAPP secretion. The data further demonstrates that PKC activation mediates the effect of the bryostatin on sAPP secretion. (see FIGS. 1-3)

Macrocyclic lactones, and particularly bryostatin-1 is described in U.S. Pat. No. 4,560,774. Macrocyclic lactones and their derivatives are described elsewhere in the art for instance in U.S. Pat. No. 6,187,568, U.S. Pat. No. 6,043,270, U.S. Pat. No. 5,393,897, U.S. Pat. No. 5,072,004, U.S. Pat. No. 5,196,447, U.S. Pat. No. 4,833,257, and U.S. Pat. No. 4,611,066. The above patents describe various compounds and various uses for macrocyclic lactones including their use as an anti-inflammatory or anti-tumor agent. Other discussions regarding bryostatin class compounds can be found in: Differential Regulation of Protein Kinase C Isozymes by Bryostatin 1 and Phorbol 12-Myristate 13-Acetate in NIH 3T3 Fibroblasts, Szallasi et al., Journal of Biological Chemistry, Vol. 269, No. 3, pp. 2118-24 (1994); Preclinical Pharmacology of the Natural Product Anticancer Agent Bryostatin 1, an Activator of Protein Kinase C, Zhang et al., Cancer Research 56, 802-808 (1996); Bryostatin 1, an activator of protein kinase C, inhibits tumor promotion by phorbol esters in SENCAR mouse skin, Hennings et al., Carcinogenesis vol. 8, no. 9, pp 1343-46 (1987); Phase II Trial of Bryostatin 1 in Patients with Relapse Low-Grade Non-Hodgkin's Lymphoma and Chronic Lymphocytic Leukemia, Varterasian et al., Clinical Cancer Research, Vol. 6, pp. 825-28 (2000); and Review Article: Chemistry and Clinical Biology of the Bryostatins, Mutter et al., Bioorganic & Medicinal Chemistry 8, pp. 1841-1860 (2000).

Macrocyclic lactones, including the bryostatin class, represent known compounds, originally derived from *Bugula neritina* L. While multiple uses for macrocyclic lactones, particularly the bryostatin class are known, the relationship between macrocyclic lactones and cognition enhancement was previously unknown.

The examples of the compounds that may be used in the present invention include macrocyclic lactones (i.e. bryostatin class and neristatin class compounds). While specific embodiments of these compounds are described in the examples and detailed description, it should be understood that the compounds disclosed in the references and derivatives thereof could also be used for the present compositions and methods.

As will also be appreciated by one of ordinary skill in the art, macrocyclic lactone compounds and their derivatives, particularly the bryostatin class, are amenable to combinatorial synthetic techniques and thus libraries of the compounds can be generated to optimize pharmacological parameters, including, but not limited to efficacy and safety of the compositions. Additionally, these libraries can be assayed to determine those members that preferably modulate α-secretase and/or PKC.

Combinatorial libraries high throughput screening of natural products and fermentation broths has resulted in the discovery of several new drugs. At present, generation and screening of chemical diversity is being utilized extensively as a major technique for the discovery of lead compounds, and this is certainly a major fundamental advance in the area of drug discovery. Additionally, even after a "lead" compound has been identified, combinatorial techniques provide for a valuable tool for the optimization of desired biological activity. As will be appreciated, the subject reactions readily lend themselves to the creation of combinatorial libraries of compounds for the screening of pharmaceutical, or other biological or medically-related activity or material-related qualities. A combinatorial library for the purposes of the present invention is a mixture of chemically related compounds, which may be screened together for a desired property; said libraries may be in solution or covalently linked to a solid support. The preparation of many related compounds in a single reaction greatly reduces and simplifies the number of screening processes that need to be carried out. Screening for the appropriate biological property may be done by conventional methods. Thus, the present invention also provides methods for determining the ability of one or more inventive compounds to bind to effectively modulate α-secretase and/or PKC.

A variety of techniques are available in the art for generating combinatorial libraries described below, but it will be understood that the present invention is not intended to be limited by the foregoing examples and descriptions. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS1 1 6:266 1: Kerr et al. (I 993) JACS I 1 5:252; PCT publications W092/10092, W093/09668 and W091/07087; and the Lemer et al. PCT publication W093/20242). Accordingly, a variety of libraries on the order of about 16 to 1,000,000 or more diversomers can be synthesized and screened for a particular activity or property.

The present compounds can be administered by a variety of routes and in a variety of dosage forms including those for oral, rectal, parenteral (such as subcutaneous, intramuscular and intravenous), epidural, intrathecal, intra-articular, topical and buccal administration. The dose range for adult human beings will depend on a number of factors including the age, weight and condition of the patient and the administration route.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening or emulsifying agents can be included.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injection may contain, together with the active compound, a pharmaceutically acceptable carrier such as sterile water, olive oil, ethyl oleate, glycols such as propylene glycol and, if desired, a suitable amount of lidocaine hydrochloride. Solutions for intravenous injection or infusion may contain a carrier, for example, sterile water that is generally Water for Injection. Preferably, however, they may take the form of a sterile, aqueous, isotonic saline solution. Alternatively, the present compounds may be encapsulated within liposomes. The present compounds may also utilize other known active agent delivery systems.

The present compounds may also be administered in pure form unassociated with other additives, in which case a capsule, sachet or tablet is the preferred dosage form.

Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

All books, articles, or patents references herein are incorporated by reference to the extent not inconsistent with the present disclosure. The present invention will now be described by way of examples, which are meant to illustrate, but not limit, the scope of the invention.

EXAMPLES

Example I

Materials And Methods

Cell Culture

Cultured skin fibroblasts were obtained from the Coriell Cell Repositories and grown using the general guidelines established for their culture with slight modifications (Cristofalo & Carptentier, 1988; Hirashima et al., 1996). The culture medium in which cells were grown was Dulbecco's modified Eagle's medium (GIBCO) supplemented with 10% fetal calf serum (Biofluids, Inc.). Fibroblasts from control cell lines (AC), cases AG07141 and AG06241, and a familial AD (FAD) case (AG06848) were utilized.

PKC Activators

The different tissue distributions, the apparently distinctive roles of different isozymes, and the differential involvement in pathology make it important to use pharmacological tools that are capable of preferentially targeting specific isozymes (Kozikowski et al., 1997; Hofmann, 1997). Recent research in the medicinal chemistry field has resulted in the development of several PKC activators, for instance different benzolactams and pyrollidinones. However, the currently studied bryostatin PKC activator not only has the benefit of providing isospecific activity, but also does not suffer from the set back of the previously used PKC activator, such as being tumor promoting. The bryostatin competes for the regulatory domain of PKC and engages in very specific hydrogen bond interactions within this site. Additional information on the organic chemistry and molecular modeling of this compound can be found throughout the literature.

Treatment

Cells grown to confluence in 6 cm Petri dishes for 5-7 days. On the day of the experiment, medium was replaced with DMEM without serum and left undisturbed for 2 h. Upon completion of the 2 hour serum deprivation, treatment was achieved by direct application to the medium of Bryo, BL and DMSO at the appropriate concentrations. DMSO was less than 1% in all cases. In most cases, medium was collected and processed after 3 hours of treatment for sAPP secretion. Other time points were also used to establish a time course of secretion.

Immunoblot Assay

Immunoblot experiments were conducted using well-established procedures (Dunbar, 1994). Cells were grown to confluency (~90%) in 6 cm Petri dishes. Levels of isozyme in response to treatment with 0.1 nM bryostatin-1 for 5, 30, 60, and 120 minutes was quantified using procedures slightly modified from that established by Racchi et al., (1994). Fibroblasts were washed twice with ice-cold PBS, scraped in PBS, and collected by low-speed centrifugation. The pellets were re-suspended in the following homogenization buffer: 20 mM Tris-HCl, pH 7.5, 2 mM EDTA, 2 mM EGTA, 5 mM DTT, 0.32 M sucrose, and protease inhibitor cocktail (Sigma). Homogenates were obtained by sonication, and centrifuged at ~12,000 g for 20 minutes, and the supernatants were used as the cytosolic fraction. The pellets were homogenized in the same buffer containing 1.0% Triton X-100, incubated in ice for 45 minutes, and centrifuged at ~12,000 g for 20 minutes. The supernatant from this batch was used as the membranous fraction. After protein determination, 20 μg of protein were diluted in 2× electrophoresis sample buffer (Novex), boiled for 5 minutes, run on 10% acrylamide gel, and transferred electrophoretically to a PVDF membrane. The membrane was saturated with 5% milk blocker by incubating it at room temperature for an hour. The primary antibody for PKC isoform (Transduction Laboratories) was diluted (1:1000) in blocking solution and incubated with the membrane overnight at 4° C. After incubation with the secondary antibody, alkaline phosphatase antimouse IgG (Vector Laboratories), the membrane was developed using a chemoluminescent substrate (Vector Laboratories) per the manufacturer's instructions. The band intensities were quantified by densitometry using a BioRad GS-800 calibrated scanning densitometer and Multianalyst software (BioRad).

sAPP—Determinations.

The concentration of secreted APP was measured using conventional immunoblotting techniques, with minor modifications the protocol. Precipitated protein extracts from each dish/treatment were loaded to freshly prepared 10% acrylamide Tris HCl minigels and separated by SDPAGE. The volume of sample loaded was corrected for total cell protein per dish. Proteins were then electrophoretically transferred to PVDF membranes. Membranes were saturated with 5% non-fat dry milk to block non-specific binding. Blocked membranes were incubated overnight at 4° C. with the commercially available antibody 6E10 (1:500), which recognizes sAPP-alpha in the conditioned medium (SENETEK). After washing, the membranes were incubated at room temperature with horseradish peroxidase conjugated anti-mouse IgG secondary antibody (Jackson's Laboratories). The signal was then detected using enhanced chemiluminescence followed by exposure of Hyperfilm ECL (Amersham). The band intensities were quantified by densitometry using a BioRad GS-800 calibrated scanning densitometer and Multianalyst software (BioRad).

Figure 7:
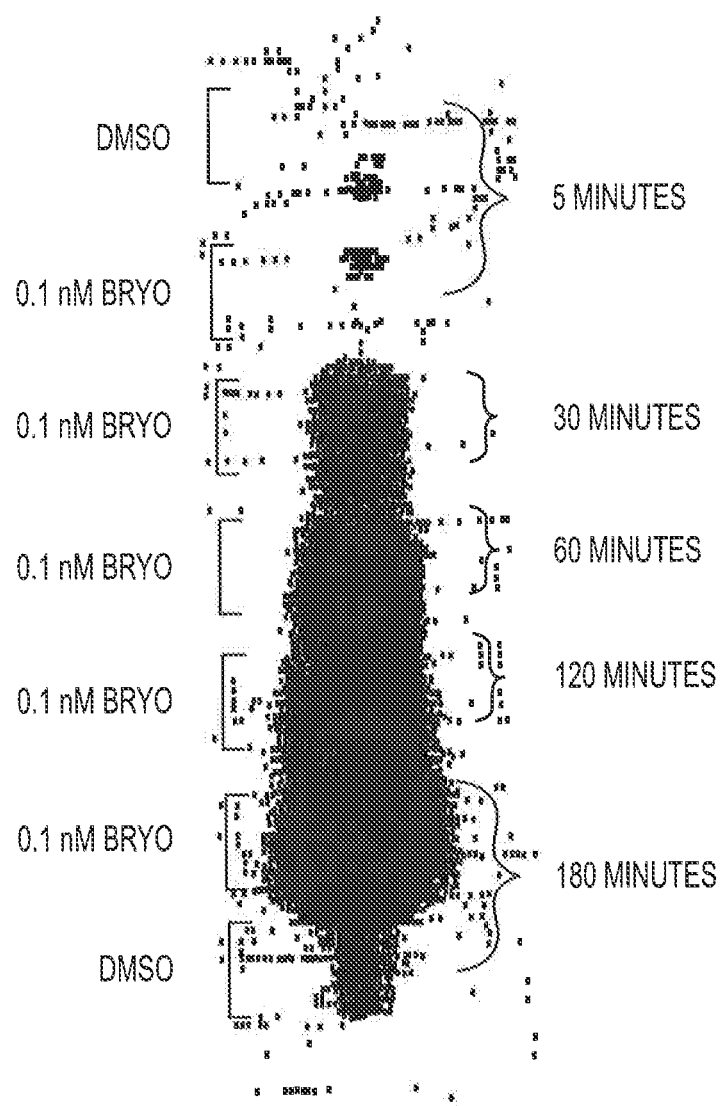
FIG. 7 illustrates an immunoblot for sAPP following administration of bryostatin in AD cells.

As shown in FIG. 7, Bryostatin-1 elicits a powerful response, demonstrating the activation of PKC, It should be noted the activation of PKC is easily detectable 30 minutes after delivery, following a dose of only 0.1 nM of bryostatin-1.

It is also interesting to consider the data in relation to APP metabolism and the effects of its sub-products. Studies have demonstrated that PKC activation increases the amount of ratio of non-amyloidogenic (soluble APP, presumably product of the secretase) vs. amyloidogenic (A$\beta$1-40 and/or A$\beta$1-42) secreted fragments (Buxbaum et al., 1990; Gillespie et al., 1992; Selkoe, 1994). Without wishing to be held to this theory, one could speculate that AD cells with low PKC would have an impaired secretion of sAPP and/or have increased proportion of amyloidogenic fragments. Indeed, there is evidence that some AD cell lines exhibit both defective PKC and impaired sAPP secretion (Bergamaschi et al., 1995; Govoni et al., 1996). In addition, $\beta$-amyloid has been shown to induce an AD-like $K^+$ channel defect in fibroblasts (Etcheberrigaray et al., 1994) and to block $K^+$ currents in cultured neurons (Good et al., 1996). Therefore, we suggest a mechanistic link such that an isozyme-specific PKC defect may lead to abnormal APP processing that, among other possible deleterious effects, alters $K^+$ channel function. Recent preliminary data also suggest that, perhaps in a vicious cyclical manner, $\beta$-amyloid in turn causes reductions of PKC (Favit et al., 1997).

In summary, the data suggest that the strategy to up-regulate PKC function targeting specific isozymes increases sAPP production. These studies and such a fibroblast model could be expanded and used as tools to monitor the effect of compounds (brysotatin, for example) that alter potential underlying pathological processes. Further, one of ordinary skill in the art would know how to further test these samples through $Ca^{2+}$ imagining and electrophysiology. Such compounds could then be used as bases for rational design of pharmacological agents for this disorder.

Example II

Figure 4:
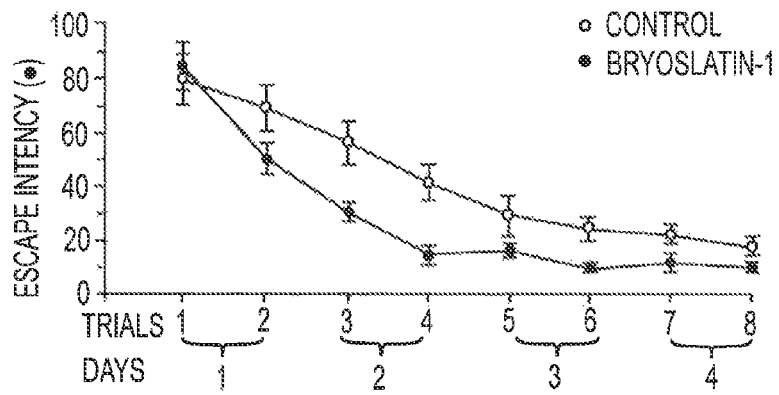
FIG. 4 illustrates the amount of time required for treated rats verse controls to learn a water maze.
Figure 5A:
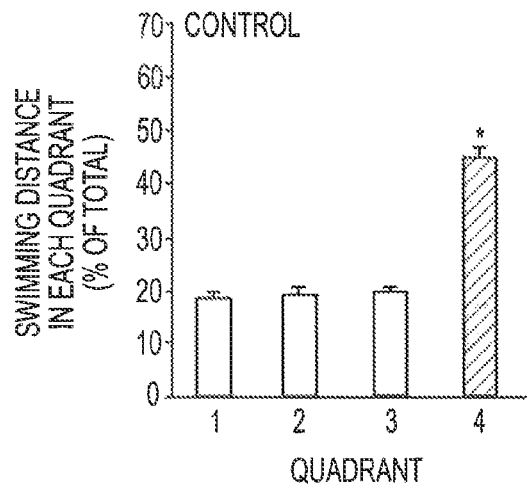
FIG. 5($a$) illustrates the amount of time control rats spent swimming in the different quadrants.
Figure 5B:
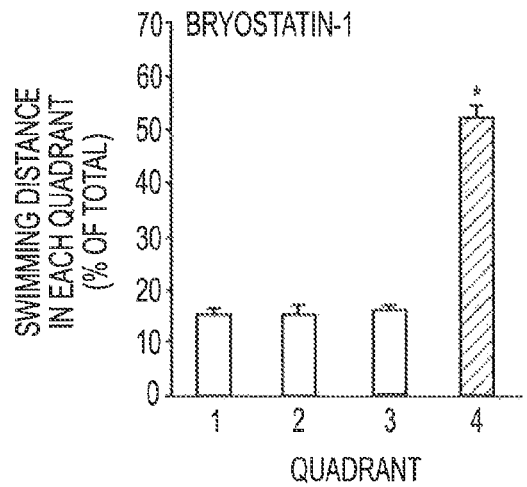
Figure 5C:
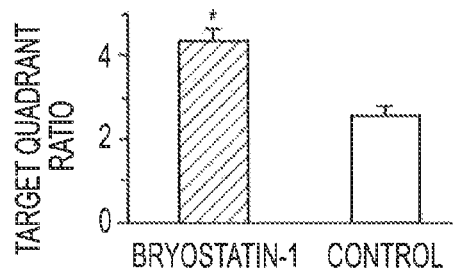
Figure 6:
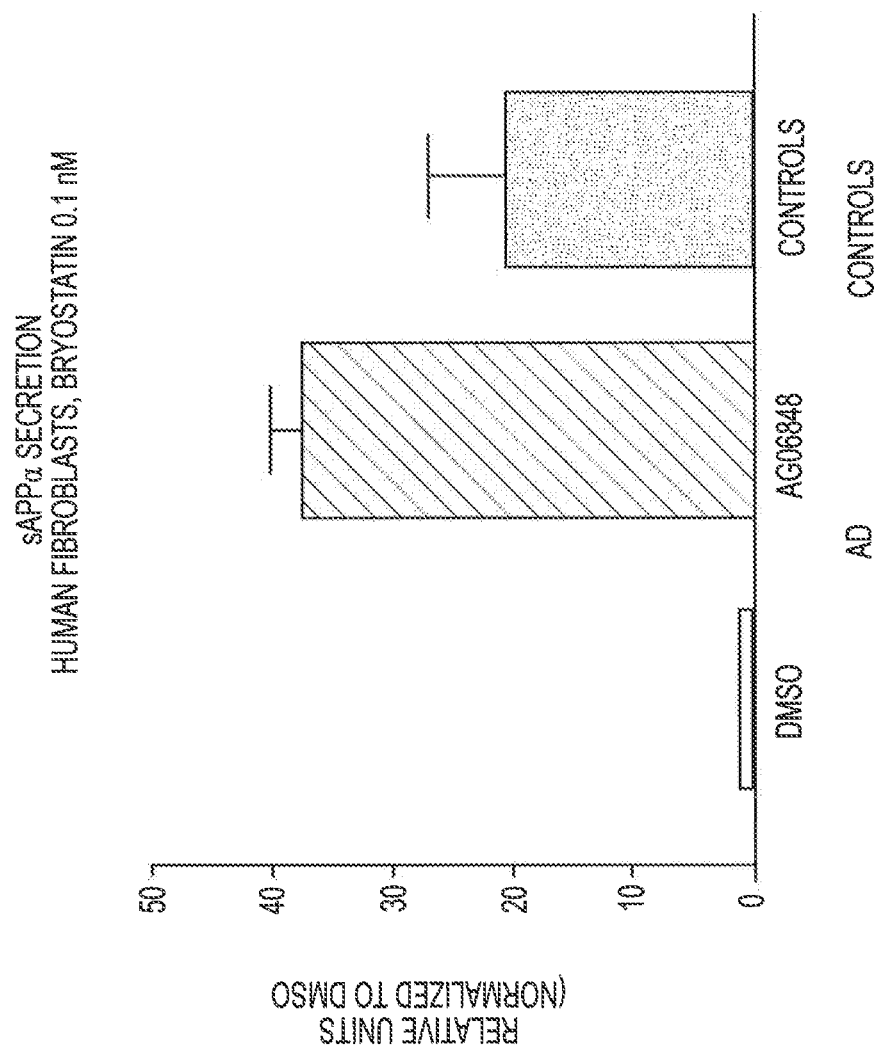
FIG. 6 illustrates sAPPα secretion in human fibroblast cells following administration of bryostatin 0.1 nM for both controls and AD cells.

The effect of PKC activators on cognition was demonstrated by the Morris Water Maze paradigm. In the present example, rats were injected intraventricularly with bryostatin-1 and trained for 4 days (following standard protocols). Retention was assessed on the $5^{th}$ day. Learning was measured as the reduction of escape latency from trial to trial, which was significantly lower in the treated animals. Acquisition of memory was measured as time spent in the relevant quadrant ($5^{th}$ day). Memory or retention was significantly enhanced in treated animals, compared to sham injection animals (see FIGS. 4 through 5(a)-5(c)). The rats treated with bryostatin-1 showed improved cognition over control rats within 2 days of treatment (see FIG. 4). Bryostatin-1 is capable of being used at concentrations to improve cognition that are 300 to 300,000 times lower than the concentration used to treat tumors. The above example further shows that cognitive ability can be improved in non-diseased subjects as compared to other non-diseased subjects through the administration of bryostatin-1.

Because of the previously conducted safety, toxicology and phase II clinical studies for cancer, one can conclude that the use of PKC activators, particularly bryostatin-1, would be viewed as safe and that phase II studies for AD treatment/cognitive enhancement could be expedited. Furthermore, bryostatin-1's lipophilic nature provides increased blood brain barrier transport. The present invention would allow for intravenous, oral, intraventricular, and other known methods of administration.

Test of sAPP secretion experiments, PKC activation experiments, and animal behavior experiments have shown that increases in sAPP secretion follow increased PKC activation and result in improved cognition in animal behavior studies.

What is claimed is:

1. A method for treating Alzheimer's disease, comprising administering a macrocyclic lactone chosen from bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, and bryostatin 18 in a pharmaceutically acceptable carrier to a human patient in an amount effective to treat Alzheimer's Disease.

2. A method for enhancing cognitive ability in a human or animal subject with the Lewy-body variant of Alzheimer's disease with or without association with Parkinson's disease, comprising administering to the human or animal subject a macrocyclic lactone chosen from bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, and bryostatin 18 in a pharmaceutically acceptable carrier in an amount effective to treat cognitive impairment in the human or animal subject with the Lewy-body variant of Alzheimer's disease with or without association with Parkinson's disease.

* * * * *